United States Patent
Arentsen et al.

(10) Patent No.: US 8,703,706 B2
(45) Date of Patent: Apr. 22, 2014

(54) CLOSED CONTAINER COMPRISING AN ACTIVATED FACTOR VII POLYPEPTIDE, PROCESSES FOR THE PREPARATION OF THE SAME, AND A KIT AND A METHOD FOR USE OF THE KIT

(75) Inventors: Anne Charlotte Arentsen, Holte (DK); Per Kaersgaard, Naerum (DK)

(73) Assignee: Novo Nordisk Healthcare AG, Zurich (CH)

(*) Notice: Subject to any disclaimer, the term of this patent is extended or adjusted under 35 U.S.C. 154(b) by 1135 days.

(21) Appl. No.: 11/912,699

(22) PCT Filed: Apr. 28, 2006

(86) PCT No.: PCT/EP2006/061921
§ 371 (c)(1),
(2), (4) Date: Apr. 29, 2008

(87) PCT Pub. No.: WO2006/114448
PCT Pub. Date: Nov. 2, 2006

(65) Prior Publication Data
US 2008/0206225 A1 Aug. 28, 2008

Related U.S. Application Data

(60) Provisional application No. 60/679,041, filed on May 9, 2005.

(30) Foreign Application Priority Data

Apr. 28, 2005 (DK) .................................. 2005 00619

(51) Int. Cl.
*A61K 38/43* (2006.01)
*A61K 38/48* (2006.01)
*C07K 14/745* (2006.01)

(52) U.S. Cl.
CPC ............ *A61K 38/4846* (2013.01); *C07K 14/745* (2013.01); *C12Y 304/21021* (2013.01)
USPC ........ 514/14.3; 514/13.5; 514/13.7; 530/412; 530/416

(58) Field of Classification Search
None
See application file for complete search history.

(56) References Cited

U.S. PATENT DOCUMENTS

| 4,637,932 | A | * | 1/1987 | Pancham ........................ 530/381 |
| 5,176,635 | A | | 1/1993 | Dittmann | |
| 5,633,350 | A | | 5/1997 | Fischer et al. | |
| 6,310,183 | B1 | | 10/2001 | Johannessen et al. | |
| 2004/0003789 | A1 | | 1/2004 | Kreuter | |
| 2004/0009918 | A1 | | 1/2004 | Nedergaard et al. | |
| 2004/0037893 | A1 | * | 2/2004 | Hansen et al. ................. 424/682 |

FOREIGN PATENT DOCUMENTS

| JP | 1171302 A | 7/1989 |
| JP | 3155797 | 7/1991 |
| JP | 0614975 | 1/1994 |
| WO | WO 94/07510 | 4/1991 |
| WO | WO 01/22972 | 4/2001 |
| WO | 03/055531 A2 | 7/2003 |
| WO | WO 03/055512 | 7/2003 |
| WO | WO 04/000347 | 12/2003 |
| WO | WO 2004/082708 | 9/2004 |
| WO | WO 2004/083421 | 9/2004 |
| WO | WO 2004/101740 | 11/2004 |
| WO | WO 2004/112828 | 12/2004 |
| WO | 2005/002615 A1 | 1/2005 |
| WO | WO 2005/016365 | 2/2005 |
| WO | WO 2005/058283 | 6/2005 |
| WO | WO 2006074664 A1 * | 7/2006 |

OTHER PUBLICATIONS

Weinstein et al., Thrombosis Research 1990, 59:759-772.*
Williams et al., Ion-Exchange Chromatography, in Current Protocols in Protein Science (1999) 8.2.1-8.2.30).*
Shire et al., J Pharm Sci. Jun. 2004;93(6):1390-402.*
Trevino et al., J Pharm Sci. Oct. 2008;97(10):4155-66. doi: 10.1002/jps.21327.*
Stennicke et al., Haemophilia, 2010, vol. 16, Suppl. 4, pp. 1-158.
Wang, International Journal of Pharmaceutics, 2000, vol. 203, pp. 160.
Mollerup, I. et al., The Use of RP-HPLC for measuring activation and cleavage of rFVIIa during purification, Biotechnology and Bioengineering, vol. 48 (5), pp. 501-505 (1995).
Hansen, T.B., et al., Studies on coagulation factor VIIa autoproteolysis and formation of degradation products, Poster presented at ACS, 2003.

* cited by examiner

Primary Examiner — Michael Szperka
(74) Attorney, Agent, or Firm — Rosemarie R. Wilk-Orescan

(57) ABSTRACT

The present invention relates to a closed container holding a composition of an activated Factor VII polypeptide in an amount of in the range of 2.5-90 mg per imL volume of the container. The invention also relates to various processes for the preparation of such closed containers, a kit including such containers and a method of using the kit.

16 Claims, 1 Drawing Sheet

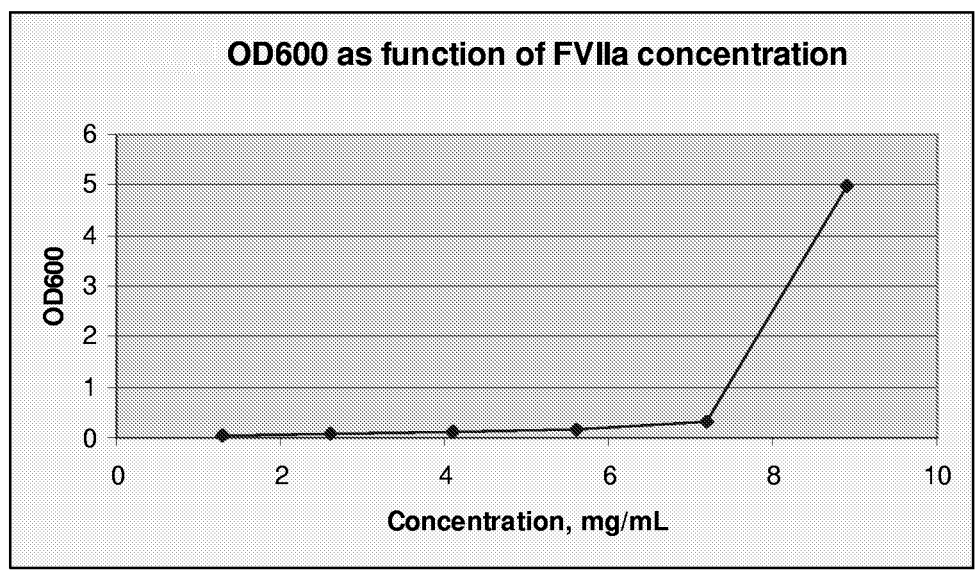

CLOSED CONTAINER COMPRISING AN ACTIVATED FACTOR VII POLYPEPTIDE, PROCESSES FOR THE PREPARATION OF THE SAME, AND A KIT AND A METHOD FOR USE OF THE KIT

CROSS-REFERENCE TO RELATED APPLICATIONS

This application is a 35 U.S.C. §371 national stage application of International Patent Application PCT/EP2006/061921 (published as WO 2006/11448), filed Apr. 28, 2006, which claimed priority of Danish Patent Application PA 2005 00619, filed Apr. 28, 2005; this application further claims priority under 35 U.S.C. §119 of U.S. Provisional Application 60/679,041, filed May 9, 2005.

FIELD OF THE INVENTION

The present invention relates to a closed container holding a composition of an activated Factor VII polypeptide in an amount of in the range of 2.5-90 mg per mL volume of the container. The invention also relates to various processes for the preparation of such closed containers, a kit including such containers and a method of using the kit.

BACKGROUND OF THE INVENTION

Factor VII, which is involved in the clotting cascade has proven to be a useful therapeutic agent to treat a variety of pathological conditions. Accordingly, there is an increasing need for formulations comprising activated Factor VII polypeptides that are pharmaceutically acceptable and exhibit a uniform and predetermined clinical efficacy. For certain therapeutic applications, it is necessary to administer a fairly large amount of an activated Factor VII polypeptide, e.g. in the order of 40 µg/kg body weight or even more.

The current commercially available, recombinantly-made Factor VII polypeptide composition NovoSeven® (Novo Nordisk A/S, Denmark), is, e.g., presented as a vial (about 3.0 mL container volume) containing 1.2 mg recombinant human Factor VIIa, 5.84 mg NaCl, 2.94 mg $CaCl_2$, $2H_2O$, 2.64 mg GlyGly, 0.14 mg polysorbate 80, and 60.0 mg mannitol. This product is reconstituted to pH 5.5 by 2.0 mL water for injection (WFI) prior to use, thus yielding a concentration of the Factor VII polypeptide of about 0.6 mg/mL.

For therapeutic applications where administration of larger amounts (e.g. 10-20 mg) of an activated Factor VII polypeptide (e.g. recombinantly-made human Factor VIIa) is necessary, it is inconvenient to utilize a formulation like the NovoSeven® composition, because a fairly large volume (e.g. 15-30 mL) needs to be administered, typically by injection.

Thus, there is a need for liquid pharmaceutical products, as well as freeze-dried pharmaceutical products for subsequent reconstitution, comprising an activated Factor VII polypeptide in which a relatively high amount of the activated Factor VII polypeptide is present within a certain container volume, whereby the volume to be administered, typically by injection, causes a minimum of inconvenience for the end-user.

WO 03/055512 A1 discloses a liquid, aqueous composition comprising (i) a factor VII polypeptide; (ii) an agent suitable for keeping pH in the range of from about 4.0 to about 8.0; (iii) an agent selected from the list of: a calcium salt, a magnesium salt, or a mixture thereof; wherein the concentration of (iii) is at least 15 mM. The invention disclosed in the international patent application appears to be applicable for Factor VII polypeptides in various concentration ranges, including a concentration range of from about 0.1 mg/mL to about 10 mg/mL.

WO 2004/000347 A1 i.a. discloses a composition which, when dissolved in water, comprises a Factor VII polypeptide (0.6 to 10 mg/mL), calcium chloride (5 to 20 mM), NaCl (0-50 mM), glycylclycine (0-15 mM), L-histidine (0-20 mM), mannitol (20-40 mg/mL), sucrose (5-20 mg/mL), methionine (0-1 mg/mL), poloxamer 188 (0.5-3 mg/mL), at a pH in the range of 5.0 to 7.0.

WO 2004/082708 A1 discloses a liquid, aqueous pharmaceutical composition comprising a Factor VII polypeptide (0.1-10 mg/mL) and a buffering agent suitable for keeping pH in the range of from about 5.0 to about 9.0; wherein the molar ratio of non-complexed calcium ions (Ca2+) to the Factor VII polypeptide is lower than 0.5.

WO 2004/112828 A1 discloses a liquid, aqueous composition comprising (i) a factor VII polypeptide; (ii) an agent suitable for keeping pH in the range of from about 4.0 to about 8.0; (iii) an agent selected from the list of: a calcium salt, a magnesium salt, or a mixture thereof; wherein the concentration of (iii) is less than 15 mM; and (iv) an ionic strength modifying agent; wherein the ionic strength of the composition is at least 200 mM. The invention disclosed in the international patent application appears to be applicable for Factor VII polypeptides in various concentration ranges, including a concentration range of from about 0.1 mg/mL to about 10 mg/mL.

WO 2005/016365 A1 discloses a liquid, aqueous pharmaceutical composition comprising at least 0.01 mg/mL of a Factor VII polypeptide (i); a buffering agent (ii) suitable for keeping pH in the range of from about 5.0 to about 9.0; and at least one stabilising agent (iii) comprising a —C(=N—$Z^1$—$R^1$)—NH—$Z^2$—$R^2$ motif (e.g. a benzamidine or an arginine). The invention disclosed in the international patent application appears to be applicable for Factor VII polypeptides in various concentration ranges, including a concentration range of 0.01-20 mg/mL.

Although several of the applicant's prior patent applications encompass the option of utilizing the respective invention for liquid solutions of a Factor VII polypeptide in fairly broad concentration range, the working examples thereof have not explored the upper region of such concentration ranges, neither has any of the prior patent applications disclosed or anticipated a closed container comprising a relatively high amount of an activated Factor VII polypeptide. It is believed that this is due to the general understanding that the degree of degradation of a Factor VII polypeptide, in particular heavy-chain degradation, will increase dramatically with increasing Factor VII polypeptide concentration, regardless of the general measures applied with the purpose of reducing the autocatalytic degradation of the activated Factor VII polypeptide, and that a high degree of degradation will yield products that are unacceptable for most therapeutic applications.

Furthermore, it is believed that the fact that the prior art commercial product comprises relatively high amounts of calcium may become problematic when large amounts of the active ingredient (the Factor VII polypeptide) are necessary for the treatment of particular conditions. High amounts of calcium may therefore necessitate high concentrations of Factor VII polypeptide in a small volume.

To be able to obtain a closed container with a high content of an activated Factor VII polypeptide per volume unit of the container, a highly concentrated bulk of purified, activated Factor VII polypeptide that can be dispensed into the container is required. Up till now this has been considered difficult or even impossible because activated Factor VII polypeptide is a serine protease that possesses autoproteolytic activity, which means that the protein catalyses the degradation of itself (see e.g. "The Use of RP-HPLC for measuring activation and cleavage of rFVIIa during purification" by I. Mollerup et al., Biotechnol. Bioeng., vol. 48 (1995), 501-505 and "Studies on coagulation factor VIIa autoproteolysis and formation of degradation products' by T. B. Hansen et al., poster presented at ACS (2003)". The degradation is caused by cleavage in the C-terminal side of Lys38, Arg290 and Arg315. By cleavage, the protein looses its haemostatic function, and thus its therapeutic effect. The degradation rate is proportional to the concentration of the activated Factor VII polypeptide in the second order as follows:

$$-d[FVIIa]/dt=k[FVIIa]^2$$

where [FVIIa] is the concentration of the activated Factor VII polypeptide.

This means that if the activated Factor VII polypeptide is concentrated e.g. 10 times, then the degradation rate is expected to increase 100 times.

Another difficulty of concentrating an activated Factor VII polypeptide is its solubility, which means that the activated Factor VII polypeptide will start to precipitate when it reaches a certain concentration in any given buffer.

BRIEF DESCRIPTION OF THE INVENTION

The present inventors have now surprisingly found that it is indeed possible to prepare a convenient pharmaceutical product (e.g. a vial, carpule, etc.) with a relevant, high amount of an activated Factor VII polypeptide in that the degree of autocatalytic degradation, in particular heavy-chain degradation of the activated Factor VII polypeptides can be suppressed by suitable selection of conditions, and that the degree of degradation is lower than expected.

Thus, a first aspect of the present relates to a closed container holding a composition of an activated Factor VII polypeptide (i), said container comprising in the range of 2.5-90 mg of the activated Factor VII polypeptide per mL volume of the container.

Second aspects of the present invention relates to processes for the preparation of a closed container comprising an activated Factor VII polypeptide.

A third aspect of the present invention relates to a kit comprising (i) a closed first container containing a solid pharmaceutical composition of an activated Factor VII polypeptide and (ii) a second container containing a liquid, aqueous solvent for said solid pharmaceutical composition, wherein the first container holds a composition comprising in the range of 2.5-90 mg of the activated Factor VII polypeptide per mL volume of the first container.

A fourth aspect of the present invention relates to a method for the preparation of a ready-to-use liquid, aqueous pharmaceutical composition of an activated Factor VII polypeptide from a kit as defined herein, the method comprising mixing the solid pharmaceutical composition of the first container with at least a fraction of the liquid, aqueous solvent of the second container so as to form the ready-to-use liquid, aqueous pharmaceutical composition of an activated Factor VII polypeptide.

LIST OF FIGURES

FIG. 1 shows the optical density $OD_{600}$ as a function of FVIIa concentration (mg/mL).

DETAILED DESCRIPTION OF THE INVENTION

As mentioned above, the present invention provides a closed container holding a composition of an activated Factor VII polypeptide (i), said container comprising in the range of 2.5-90 mg of the activated Factor VII polypeptide per mL volume of the container.

The term "closed" means that the content of the container is separated from the exterior. Thus, the container is typically constructed in such a way that a seal needs to be broken or a cap needs to be removed before the content of the container becomes accessible. In preferred embodiments, the container is water and gas tight, e.g. the container is also air-tight so that air or moisture cannot enter the interior of the container and thereby provoke degradation of the content. The void space of the container may be filled with an inert gas. The inert gas may be selected from the groups consisting of nitrogen, argon, etc.

The container (e.g. vial, carpule or cartridge (such as a carpule or cartridge for a pen applicator)) is typically made of glass or plastic, in particular glass, optionally closed by a rubber septum or other closure means allowing for penetration with preservation of the integrity of the pharmaceutical composition. In an embodiment, the container is a vial, carpule or cartridge enclosed in a sealed bag, e.g. a sealed plastic bag, such as a laminated (e.g. metal (such as aluminium) laminated plastic bag). In an interesting variant, the container has an inner wall material selected from silica-coated glass, silicone-coated glass, polymers of non-cyclic olefins, cycloolefin polymers, and cycloolefin/linear olefin copolymers, e.g. as disclosed in the applicant's earlier application WO 2004/103398.

When used herein, the term "product" refers to the container including the composition of the activated Factor VII polypeptide. I.e. the term "product" is typically the commercial product sold, such as a vial, carpule or cartridge holding a composition of an activated Factor VII polypeptide.

The term "composition" refers to a solid or liquid mixture which includes the activated Factor VII polypeptide and optionally one or more additives, e.g. buffers, stabilising agents, tonicity modifying agents, etc. (see below).

The activated Factor VII polypeptide is as defined further below.

The term "mL volume of the container" is intended to refer to the inner volume of the container in question stated as milli liters (mL), i.e. the volume of the compartment of the container wherein the Factor VII polypeptide is present. The volume of the closed (e.g. sealed) container can be defined most accurately as the volume of void space of the corresponding closed and empty container, i.e. the container volume not occupied by the stopper, seal or the like. For example, the current commercially available, recombinantly-made Factor VII polypeptide composition NovoSeven® (Novo Nordisk A/S, Denmark), is presented in three differently sized vials, (i) 4.3 mL+0.5 mL of volume, (ii) 7.1 mL+0.5 mL of volume, and (iii) 13.5 mL±1.0 mL of volume. In these vials the stopper occupies 0.44 mL of the container volume, i.e., the void space of the corresponding closed and empty containers are (i) 3.86 mL+0.5 mL, (ii) 6.66 mL+0.5 mL, and (iii) 13.06 mL+1.0 mL.

The container typically comprises in the range of 2.5-90 mg, such as in the range of 2.5-75 mg or in the range of 4-90 mg, of the activated Factor VII polypeptide per mL volume of the container. In some embodiments, the container comprises 4-60 mg per mL volume, such as 4-50 mg per mL volume, or 5-25 mg per mL volume, or 6-15 mg per mL volume. In other embodiments, the container comprises 2.5-60 mg per mL volume, such as 2.5-50 mg per mL volume, or 2.5-40 mg per mL volume, or 2.5-30 mg per mL volume. For some therapeutic applications, the container may comprise 4-15 mg per mL volume, or 6-40 mg per mL volume, or 10-30 mg per mL volume or 25-60 mg per mL volume.

The composition of the activated Factor VII polypeptide may be in either solubilized form, e.g. as an aqueous solution or a suspension, or in dry form, e.g. in lyophilized form.

Composition in Solubilized Form

In one embodiment, the activated Factor VII polypeptide is in solubilized form, e.g. in aqueous solution. Preferably, the aqueous solution of the activated Factor VII polypeptide is a liquid pharmaceutical composition, in particular a ready-to-use pharmaceutical composition of the activated Factor VII polypeptide.

The term "aqueous solution" is intended to mean that the activated Factor VII polypeptide is solubilised in a solvent which is mainly constituted by water, i.e. organic solvents constitute at the most 5%, in particular at the most 2%, of the composition.

In order to render the aqueous solution useful for direct parenteral administration to a mammal such as a human, it is normally required that the pH value of the composition is held within reasonable limits, such as from about 5.0 to about 9.0. To ensure a suitable pH value under the conditions given, the pharmaceutical composition typically comprises a buffering agent (ii) suitable for keeping pH in the range of from about 5.0 to about 9.0. With the further purpose of rendering the aqueous solution more stable upon storage and handling, the solution preferably has a pH in the range of 5.0-7.0. Preferably, the pH is in the range of 5.8-6.5 or in the range of 5.5-6.2, with a particular preference for a pH in the range of 5.8-6.2.

The term "buffering agent" encompasses those agents or combinations of agents which maintain the solution pH in an acceptable range from about 5.0 to about 9.0, in particular from about 5.0 to about 6.5, such as in the range of 5.8-6.5 or in the range of 5.5-6.2, in particular in the range of 5.8-6.2. In one embodiment, the pH of the composition is kept from about 5.0 to about 6.5, from about 5.0 to about 6.0, from about 5.5 to about 6.5, from about 6.2 to about 6.5, or from about 5.7 to about 6.2, or from about 5.2 to about 5.7.

In one embodiment, the buffering agent (ii) is at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium or calcium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

The concentration of the buffering agent is chosen so as to maintain the preferred pH of the solution. In various embodiments, the concentration of the buffering agent is in the range of 1-100 mM; in the range of 1-50 mM; in the range of 1-25 mM; or in the range of 2-20 mM.

In addition to the three mandatory components (FVII polypeptide, solvent, buffering agent), the liquid, aqueous pharmaceutical composition may comprise additional components beneficial for the preparation, formulation, stability, or administration of the composition.

In order to improve the stability of the aqueous solution it is also possible to include one or more stabilising agents (iii), e.g., one or more stabilising agent(s) selected from calcium salts and magnesium salts (iiia); and/or one or more divalent first transition series metal-type stabilizing agents (iiib), wherein said metal is selected from the group consisting of first transition series metals of oxidation state +II, except zinc; and/or one or more stabilising agents (iiic) comprising a —C(=N—$Z^1$—$R^1$)—NH—$Z^2$—$R^2$ motif, wherein $Z^1$ and $Z^2$ independently are selected from the group consisting of —O—, —S—, —$NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or $Z^2$ and $R^2$ are as defined above and —C=N—$Z^1$—$R^1$ forms part of a heterocyclic ring, or $Z^1$ and $R^1$ are as defined above and —C—NH—$Z^2$—$R^2$ forms part of a heterocyclic ring, or —C(=N—$Z^1$—$R^1$)—NH—$Z^2$—$R^2$ forms a heterocyclic ring wherein —$Z^1$—$R^1$—$R^2$—$Z^2$— is a biradical.

Calcium Salts and Magnesium Salts (iiia)

In one embodiment, the stabilizing agent include(s) at least one agent selected from calcium salts and magnesium salts, in particular from calcium salts.

Examples of calcium salts are calcium chloride, calcium acetate, calcium gluconate, calcium laevulate, or a mixture thereof.

Examples of magnesium salts are magnesium chloride, magnesium acetate, magnesium sulphate, magnesium gluconate, magnesium laevulate, magnesium salts of strong acids, or a mixture thereof.

The concentration of (iiia) in the aqueous solution is preferably at least 15 mM, e.g. at least 25 mM, such as at least 50 mM, at least 100 mM, at least 200 mM, at least 400 mM, or at least 800 mM.

In preferred embodiments, the stabilising agent (iiia) is selected from calcium chloride, calcium acetate, magnesium chloride, magnesium acetate, magnesium sulphate, or a mixture thereof; and the ionic strength modifying agent (iv) is sodium chloride or a mixture of sodium chloride and at least one additional ionic strength modifying agent (see further below).

Divalent First Transition Series Metal-Type Stabilizing Agent (iiib)

In another embodiment, the stabilising agent (iii) includes at least one metal-containing agent (iiib), wherein said metal is selected from the group consisting of first transition series metals of oxidation state +II.

When used herein, the term "first transition series metals of oxidation state +II" is intended to encompass the metals titanium, vanadium, chromium, manganese, iron, cobalt, nickel, and copper.

Although titanium and vanadium may exist in oxidation state +II in aqueous environments, it is more typical to select the metal(s) among chromium, manganese, iron, cobalt, nickel, and copper. Illustrative examples of metal-containing agents (iiib) corresponding to these metals are chromium(II) chloride, manganese(II) chloride, iron(II) chloride, cobalt(II) chloride, nickel(II) chloride, and copper(II) chloride. It should be understood that the metal-containing agent (iiib) may comprise two or more metals, e.g. two or more first transition series metals.

Thus in some instances, two or more of the above-mentioned agents may be used in combination.

So far, the most promising metals are copper and manganese. Illustrative examples of corresponding metal-containing agents (iiib) are copper(II) chloride and manganese(II) chloride.

The concentration of the metal-containing agent (or agents) (iiib) is typically at least 1 µM. The desirable (or necessary) concentration typically depends on the selected metal-containing agent (or agents), more specifically on the binding affinity of the selected metal of oxidation state +II to the Factor VII polypeptide.

In different embodiments, the metal-containing agent (iiib) is present in a concentration of at least 5 µM, at least 25 µM, at least 50 µM, at least 100 µM, at least 200 µM, at least 400 µM, at least 500 µM, at least 800 µM, at least 900 µM, at least 1000 µM, at least 5 mM, at least 25 mM, at least 50 mM, at least 100 mM, at least 200 mM, at least 400 mM, at least 800 mM, at least 900 mM, or at least 1000 mM.

In various embodiments, the molar ratio between the metal-containing agent (iii) ($Me_2^+$) and FVII polypeptide (agent (iiib):FVII) is: above 0.5; above 1; above 2; above 4; above 5; above 10; above 25; above 100; above 150; such as, e.g., in the range of 0.5-250, such as 0.5-150, 0.5-100; 0.5-25; 1-250; 1-100; 1-25; 1-10.

In one particular embodiment, the metal of the metal-containing agent (iiib) is copper and the concentration of said agent is at least 5 µM, such as at least 10 µM, or at least 15 µM.

In another particular embodiment, the metal of the metal-containing agent (iiib) is manganese and the concentration of said agent is at least 100 µM, such as at least 500 µM, or at least 1 mM.

Benzamidine/Arginine Type Stabilizing Agent (iiic)

In still another embodiment, the stabilizing agent includes at least one agent (iiic) comprising a —C(=N—$Z^1$—$R^1$)—NH—$Z^2$—$R^2$ motif, wherein $Z^1$ and $Z^2$ independently are selected from the group consisting of —O—, —S—, —$NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or $Z^2$ and $R^2$ are as defined above and —C=N—$Z^1$—$R^1$ forms part of a heterocyclic ring, or $Z^1$ and $R^1$ are as defined above and —C—NH—$Z^2$—$R^2$ forms part of a heterocyclic ring, or —C(=N—$Z^1$—$R^1$)—NH—$Z^2$—$R^2$ forms a heterocyclic ring wherein —$Z^1$—$R^1$—$R^2$—$Z^2$— is a biradical.

The term "$C_{1-6}$-alkyl" is intended to encompass acyclic and cyclic saturated hydrocarbon residues which have 1-6 carbon atoms and which can be linear or branched. Particular examples are methyl, ethyl, n-propyl, isopropyl, cyclopropyl, n-butyl, isobutyl, sec-butyl, tert-butyl, cyclopropylmethyl, n-pentyl, isopentyl, n-hexyl, etc. Similarly, the term "$C_{1-4}$-alkyl" encompasses acyclic and cyclic saturated hydrocarbon residues which have 1-4 carbon atoms and which can be linear or branched.

Similarly, the term "$C_{2-6}$-alkenyl" is intended to encompass acyclic and cyclic hydrocarbon residues which have 2-6 carbon atoms and comprise one unsaturated bond, which can be linear or branched. Examples of $C_{2-6}$-alkenyl groups are vinyl, allyl, but-1-en-1-yl, but-2-en-1-yl, pent-1-en-1-yl, and hex-1-en-1-yl.

The term "optionally substituted" in connection with $C_{1-6}$-alkyl and $C_{2-6}$-alkenyl groups is intended to denote that the group in question may be substituted one or several times, preferably 1-3 times, with group(s) selected from the group consisting of hydroxy, $C_{1-6}$-alkoxy (i.e. $C_{1-6}$-alkyl-oxy), $C_{2-6}$-alkenyloxy, oxo (forming a keto or aldehyde functionality), aryl, aryloxy, arylcarbonyl, heterocyclyl, heterocyclyloxy, heterocyclylcarbonyl, amino, mono- and di($C_{1-6}$-alkyl) amino, halogen, where any aryl and heterocyclyl may be substituted as specifically described below for optionally substituted aryl and heterocyclyl.

"Halogen" includes fluoro, chloro, bromo, and iodo.

When used herein, the term "aryl" is intended to denote a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heterocyclyl" is intended to denote a saturated, partially unsaturated, partially aromatic or fully aromatic carbocyclic ring or ring system where one or more of the carbon atoms have been replaced with heteroatoms, e.g. nitrogen (=N— or —NH), sulphur (—S—), and/or oxygen (—O—) atoms. Examples of such heterocyclyl groups are oxazolyl, oxazolinyl, oxazolidinyl, isoxazolyl, isoxazolinyl, isoxazolidinyl, oxadiazolyl, oxadiazolinyl, oxadiazolidinyl, thiazolyl, isothiazolyl, pyrrolyl, pyrrolinyl, pyrrolidinyl, imidazolyl, imidazolinyl, imidazolidinyl, pyrazolyl, pyridinyl, pyrazinyl, pyridazinyl, piperidinyl, coumaryl, furyl, quinolyl, benzothiazolyl, benzotriazolyl, benzodiazolyl, benzoxozolyl, diazolyl, diazolinyl, diazolidinyl, triazolyl, triazolinyl, triazolidinyl, tetrazol, etc. Preferred heterocyclyl groups are 5-, 6- or 7-membered monocyclic groups such as isoxazolyl, isoxazolinyl, oxadiazolyl, oxadiazolinyl, pyrrolyl, pyrrolinyl, diazolyl, diazolinyl, triazolyl, triazolinyl, imidazolyl, imidazolinyl, etc.

The term "heterocyclic ring" is intended to mean a ring corresponding to those defined under "heterocyclyl".

In connection with the terms "aryl", "heterocyclyl" and "heterocyclic ring", the term "optionally substituted" is intended to denote that the group in question may be substituted one or several times, preferably 1-3 times, with group(s) selected from hydroxy (which when present in an enol system may be represented in the tautomeric keto form), $C_{1-6}$-alkyl, $C_{2-6}$-alkenyl, phenyl, benzyl, $C_{1-6}$-alkoxy, oxo (which may be represented in the tautomeric enol form), carboxy, $C_{1-6}$-alkoxycarbonyl, $C_{1-6}$-alkylcarbonyl, amino, mono- and di($C_{1-6}$-alkyl)amino, dihalogen-$C_{1-4}$-alkyl, trihalogen-$C_{1-4}$-alkyl, and halogen. The most typical examples of substituents are hydroxyl, $C_{1-4}$-alkyl, phenyl, benzyl, $C_{1-4}$-alkoxy, oxo, amino, mono- and dimethylamino and halogen.

Besides the fact that $R^1$ and $R^2$ independently can be selected from the group consisting of hydrogen, optionally substituted $C_{1-6}$-alkyl, optionally substituted $C_{2-6}$-alkenyl, optionally substituted aryl, optionally substituted heterocyclyl, it is also possible that a part of the —C(=N—$Z^1$—$R^1$)—NH—$Z^2$—$R^2$ motif may be part of a heterocyclic ring, while the other part of the motif has the meaning defined for $Z^1$, $Z^2$, $R^1$ and $R^2$, respectively. In some interesting embodiments, —C=N—$Z^1$—$R^1$ may form part of a heterocyclic ring selected from the group consisting of a 1,2-diazole ring, an isoxazole ring, a 1,2,4-triazole ring, and a 1,2,4-oxadiazole ring, or —C—NH—$Z^2$—$R^2$ may form part of a heterocyclic ring selected from the group consisting of a 1,2-diazoline ring, an isoxazoline ring, a 1,2,4-triazoline ring, and a 1,2,4-oxadiazoline ring. Such heterocyclic rings may be substituted as described above.

In some embodiments, at least one of $R^1$ and $R^2$ is hydrogen, e.g. both are hydrogen. Further, in some embodiment, which may be combined with the embodiments mentioned before, at least one of $Z^1$ and $Z^2$ is a single bond, e.g. both are a single bond. In special embodiments, $R^1$ and $R^2$ are both hydrogen, and $Z^1$ and $Z^2$ are both a single bond.

It is believed that the —C(=N—$Z^1$—$R^1$)—NH—$Z^2$—$R^2$ motif is particularly important for the stabilising effect of the stabilising agent (iiic). In particular, it is believed that the —C(=N—$Z^1$—$R^1$)—NH—$Z^2$—$R^2$ motif mimics an arginine moiety of a substrate for the Factor VII polypeptide.

In more specific embodiments, the stabilising agent (iiic) is at least one selected from the group consisting of amidine compounds comprising a —C—C(=N—$Z^1$—$R^1$)—NH—

$Z^2$—$R^2$ motif and guanidines compounds comprising a >N—C(=N—$Z^1$—$R^1$)—NH—$Z^2$—$R^2$ motif.

In some embodiments, the stabilising agent (iiic) is at least one amidine compound selected from the group consisting of benzamidines comprising the motif —$C_6H_4$—C(=N—$Z^1$—$R^1$)—NH—$Z^2$—$R^2$, wherein $C_6H_4$ denotes an optionally substituted benzene ring, of which benzamidine ($R^1$ and $R^2$ are hydrogen and $Z^1$ and $Z^2$ are a single bond) constitutes a particular embodiment.

In other particular embodiments thereof, the benzamidines comprises the motif >N—$C_6H_4$—C(=N—$Z^1$—$R^1$)—NH—$Z^2$—$R^2$, wherein $C_6H_4$ denotes an optionally substituted benzene ring, i.e. an o-amino-benzamidine, a m-amino-benzamidine or a p-amino-benzamidine, of which p-amino-benzamidines, such as p-amino-benzamidine, are the currently most promising.

Further illustrative examples of p-amino-benzamidines are those disclosed by Aventis in EP 1 162 194 A1, cf. in particular those defined in claims 1-6 and in sections [0009]-[0052], and in EP 1 270 551 A1, cf. in particular claims 1 and 2 and sections [0010]-[0032].

In another embodiment, the stabilising agent (iiic) is at least one guanidine compound selected from the group consisting of guanidines compounds comprising a —$CH_2$—NH—C(=N—$Z^1$—$R^1$)—NH—$Z^2$—$R^2$ motif. Examples of guanidine compounds are those selected from the group consisting of arginine, arginine derivatives and peptides of 2-5 amino acid residues comprising at least one arginine residue. Arginine constitutes a particular embodiment.

The term "arginine derivatives" is intended to encompass arginine homologues, N-terminal functionalised arginines (e.g. N-methylated and N-acylated (e.g. acetylated) derivatives), C-terminal functionalised arginines (e.g. C-amidated, C-alkylamidated, and C-alkylated derivatives), and combinations thereof.

As mentioned above, the one crucial motif of the stabilising agents is —C(=N—$Z^1$—$R^1$)—NH—$Z^2$—$R^2$. Other parts of the stabilising agent may also be important, in particular with respect to optimisation of the stabilising effect and the tolerance by the patient. Typically, the stabilising agent has the formula Y—C(=N—$Z^1$—$R^1$)—NH—$Z^2$—$R^2$, wherein Y is an organic radical. The radical Y is typically selected in order to improve the efficiency of the stabilising effect. Also, the radical Y may comprise one or more further motifs of the formula —C(=N—$Z^1$—$R^1$)—NH—$Z^2$—$R^2$.

The molecular weight of the stabilising agent is typically at the most 1000 Da, such as at the most 500 Da.

The concentration of the stabilising agent (or agents) (iiic) is typically at least 1 µM. The desirable (or necessary) concentration typically depends on the selected stabilising agent (or agents), more specifically on the binding affinity of the selected stabilising agent to the Factor VII polypeptide.

In different embodiments, the stabilising agent (iiic) is present in a concentration of at least 5 µM, at least 10 µM, at least 20 µM, at least 50 µM, at least 100 µM, at least 150 µM, at least 250 µM, at least 500 µM, at least 1 mM, at least 2 mM, at least 4 mM, at least 5 mM, at least 8 mM, at least 9 mM, at least 10 mM, at least 15 mM, at least 20 mM, such as in the range of 20-2000 µM, in the range of 50-5000 µM, in the range of 0.1-10 mM, in the range of 0.2-20 mM, or in the range of 0.5-50 mM.

In various embodiments, the molar ratio between the stabilising agent (iii) and FVII polypeptide (agent (iiic):FVII) is: above 0.1, above 0.5, above 1, above 2, above 5, above 10, above 25, above 100, above 250, above 1000, above 2500, or above 5000, such as, e.g., in the range of 0.1-10000, 0.1-5000, 0.1-2500, 0.1-1000, 0.1-250, 0.1-100, 0.1-25, 0.1-10, 0.5-10000, 0.5-5000, 0.5-2500, 0.5-1000, 0.5-250, 0.5-100, 0.5-25, 0.5-10, 1-10000, 1-5000, 1-2500, 1-1000, 1-250, 1-100; 1-25; 1-10, 10-10000, 10-5000, 10-250, 1000-10000, or 1000-5000.

In one embodiment, the stabilising agent (iiic) is benzamidine and the concentration of said agent is at least 0.5 mM, such as at least 2 mM, although it is envisaged that substituted benzamidines may be more potent for what reason they can be added in lower concentrations.

In one embodiment, the stabilising agent (iiic) is arginine and the concentration of said agent is at least 2 mM, such as at least 10 mM.

It should be understood that the above-mentioned stabilizing agents (iiia), (iiib) and (iiic) may be used in combination.

Other Additives

Also, the composition may further comprise a tonicity modifying agent (v).

As used herein, the term "tonicity modifying agent" includes agents which contribute to the osmolality of the solution. The tonicity modifying agent (v) includes at least one agent selected from the group consisting of neutral salts, amino acids, peptides of 2-5 amino acid residues, monosaccharides, disaccharides, polysaccharides, and sugar alcohols. In some embodiments, the composition comprises two or more of such agents in combination.

By "neutral salt" is meant a salt that is neither an acid nor a base when dissolved in an aqueous solution.

In one embodiment, at least one tonicity modifying agent (v) is a neutral salt selected from the groups consisting of sodium salts, potassium salts, calcium salts, and magnesium salts, such as sodium chloride, potassium chloride, calcium chloride, calcium acetate, calcium gluconate, calcium laevulate, magnesium chloride, magnesium acetate, magnesium gluconate, and magnesium laevulate.

In a further embodiment, the tonicity modifying agent (v) includes sodium chloride in combination with at least one selected from the groups consisting of calcium chloride, calcium acetate, magnesium chloride and magnesium acetate.

In a still further embodiment, the tonicity modifying agent (v) is at least one selected from the group consisting of sodium chloride, calcium chloride, sucrose, glucose, and mannitol.

In different embodiments, the tonicity modifying agent (v) is present in a concentration of at least 1 mM, at least 5 mM, at least 10 mM, at least 20 mM, at least 50 mM, at least 100 mM, at least 200 mM, at least 400 mM, at least 800 mM, at least 1000 mM, at least 1200 mM, at least 1500 mM, at least 1800 mM, at least 2000 mM, or at least 2200 mM.

In one series of embodiments, the tonicity modifying agent (v) is present in a concentration in the range of 5-2200 mM, such as 25-2200 mM, 50-2200 mM, 100-2200 mM, 200-2200 mM, 400-2200 mM, 600-2200 mM, 800-2200 mM, 1000-2200 mM, 1200-2200 mM, 1400-2200 mM, 1600-2200 mM, 1800-2200 mM, or 2000-2200 mM; 5-1800 mM, 25-1800 mM, 50-1800 mM, 100-1800 mM, 200-1800 mM, 400-1800 mM, 600-1800 mM, 800-1800 mM, 1000-1800 mM, 1200-1800 mM, 1400-1800 mM, 1600-1800 mM; 5-1500 mM, 25-1400 mM, 50-1500 mM, 100-1500 mM, 200-1500 mM, 400-1500 mM, 600-1500 mM, 800-1500 mM, 1000-1500 mM, 1200-1500 mM; 5-1200 mM, 25-1200 mM, 50-1200 mM, 100-1200 mM, 200-1200 mM, 400-1200 mM, 600-1200 mM, or 800-1200 mM.

In a preferred embodiment of the invention, at least one tonicity modifying agent (v) is an ionic strength modifying agent (iv).

Most preferably, the composition of the container of the invention comprises an ionic strength modifying agent (iv). Accordingly, the aqueous solution preferably comprises one or more ionic strength modifying agent(s) (iv) as well as one or more tonicity modifying agents (v) not being ion strength modifying agent(s).

As used herein, the term "ionic strength modifying agent" includes agents which contribute to the ionic strength of the solution. The agents include, but are not limited to, neutral salts, amino acids, peptides of 2 to 5 amino acid residues. In some embodiments, the composition comprises two or more of such agents in combination.

Preferred examples of ionic strength modifying agents (iv) are neutral salts such as sodium chloride, potassium chloride, calcium chloride and magnesium chloride (the latter two which may additionally be considered as "stabilising agents" (see above)). A preferred agent (iv) is sodium chloride.

The term "ionic strength" is the ionic strength of the solution ($\mu$) which is defined by the equation: $\mu=\frac{1}{2}\Sigma([i](Z_i^2))$, where $\mu$ is the ionic strength, [i] is the millimolar concentration of an ion, and $Z_i$ is the charge (+ or −) of that ion (see, e.g., Solomon, Journal of Chemical Education, 78(12):1691-92, 2001; James Fritz and George Schenk: Quantitative Analytical Chemistry, 1979).

In one embodiment of the invention, the ionic strength of the aqueous solution is at least about 50 mM, such as, e.g., at least about 100 mM. In different embodiments of the invention, the ionic strength of the aqueous solution is at least 200 mM, e.g., is at least 400 mM, such as at least 800 mM, at least 1000 mM, at least 1200 mM, at least 1500 mM, at least 1800 mM, at least 2000 mM, or at least 2200 mM. In a special variant hereof, the concentration of stabilising agent(s) (iiia) (i.e. calcium salts and magnesium salts) in the aqueous solution is less than 15 mM, however with the concurrent presence of at least 100 mM NaCl.

In some specific embodiments, the total concentration of the tonicity modifying agent (v) and the ionic strength modifying agent (iv) is in the range of 1-500 mM, such as in the range of 1-300 mM, or in the range of 10-200 mM, or in the range of 20-150 mM, depending on the effect any other ingredients may have on the tonicity and ionic strength.

In one embodiment, the composition is isotonic; in another, it is hypertonic.

The term "isotonic" means "isotonic with serum", i.e. at about 300±50 milliosmol/kg. The tonicity is meant to be a measure of osmolality of the solution prior to administration. The term "hypertonic" is meant to designate levels of osmolality above the physiological level of serum, such as levels above 300±50 milliosmol/kg.

The composition may also include a non-ionic surfactant. Surfactants (also known as detergents) generally include those agents which protect the protein from air/solution interface induced stresses and solution/surface induced stresses (e.g. resulting in protein aggregation).

Typical types of non-ionic surfactants are polysorbates, poloxamers, polyoxyethylene alkyl ethers, polyethylene/polypropylene block co-polymers, polyethyleneglycol (PEG), polyxyethylene stearates, and polyoxyethylene castor oils.

Illustrative examples of non-ionic surfactants are Tween®, polysorbate 20, polysorbate 80, Brij-35 (polyoxyethylene dodecyl ether), poloxamer 188, poloxamer 407, PEG8000, Pluronic® polyols, polyoxy-23-lauryl ether, Myrj 49, and Cremophor A.

In one embodiment, the non-ionic surfactant is present in an amount of 0.005-2.0% by weight.

In a further embodiment, the composition further comprises an antioxidant (vi). In different embodiments, the antioxidant is selected from the group consisting of L-methionine, D-methionine, methionine analogues, methionine-containing peptides, methionine-homologues, ascorbic acid, cysteine, homocysteine, gluthatione, cystine, and cysstathionine. In a preferred embodiment, the antioxidant is L-methionine.

The concentration of the antioxidant (vi) is typically in the range of 0.1-5.0 mg/mL, such as in the range of 0.1-4.0 mg/mL, in the range of 0.1-3.0 mg/mL, in the range of 0.1-2.0 mg/mL, or in the range of 0.5-2.0 mg/mL.

In particular embodiments, the composition does not include an antioxidant; instead the susceptibility of the Factor VII polypeptide to oxidation is controlled by exclusion of atmospheric air. The use of an antioxidant may of course also be combined with the exclusion of atmospheric air.

It is believed that suitable aqueous solutions useful for the containers of the invention preferably have a concentration of the activated Factor VII polypeptide of more than 5 mg/mL, or more than 6 mg/mL, such as more than 7 mg/mL, or more than 8 mg/mL, or more than 9 mg/mL, or even more than 10 mg/mL.

The solubilized composition within the container is preferably one where the activated Factor VII polypeptide is "stable" as defined herein.

Various embodiments of the closed container appear to be particularly interesting, e.g.:

(i) A container as defined herein, wherein the aqueous solution comprises:

at least 2.5 mg per mL container volume of the activated Factor VII polypeptide (i);

a buffering agent (ii) suitable for keeping pH in the range of from about 5.0 to about 6.5;

wherein the ionic strength of the aqueous solution is at least 50 mM.

(ii) A container as defined herein, wherein the aqueous solution comprises:

at least 2.5 mg per mL container volume of the activated Factor VII polypeptide (i);

a buffering agent (ii) suitable for keeping pH in the range of from about 5.0 to about 6.5;

at least one stabilising agent (iiia) selected from calcium salts in a concentration of in the range of at least 15 mM;

wherein the ionic strength of the aqueous solution is at least 50 mM;

(iii) A container as defined herein, wherein the aqueous solution comprises:

at least 2.5 mg per mL container volume of the activated Factor VII polypeptide (i);

a buffering agent (ii) suitable for keeping pH in the range of from about 5.0 to about 6.5;

at least one stabilising agent of the divalent first transition series metal-type (iiib) wherein the molar ratio between the stabilising agent (iiib) and FVII polypeptide is above 0.5;

wherein the ionic strength of the aqueous solution is at least 50 mM; and (iv) A container as defined herein, wherein the aqueous solution comprises:

at least 2.5 mg per mL container volume of the activated Factor VII polypeptide (i);

a buffering agent (ii) suitable for keeping pH in the range of from about 5.0 to about 6.5;

at least one stabilising agent of the benzamidine/arginine-type (iiic) wherein the molar ratio between the stabilising agent (iiic) and FVII polypeptide is above 0.1;

wherein the ionic strength of the aqueous solution is at least 50 mM.

Composition in Dry Form

In another embodiment, the composition is in dry form; in particular the composition has a moisture content of not more than about 3%. Preferably, the composition is in lyophilized form.

In order to stabilize the composition against degradation and shear forces in connection with the freeze-drying process, it is advantageous to include at least one stability agent, in particular at least one stability agent selected from the group consisting of a) a combination of an antioxidant and mannitol; b) a combination of methionine and a polyol; c) a combination of a saccharide and mannitol; d) a combination of sucrose and a polyol; and e) methionine.

The stabilisation of lyophilized compositions of activated Factor VII polypeptides is described in further detail in WO 2004/000347 which is hereby incorporated by reference.

Before the use of the product, the lyophilized composition is reconstituted in a liquid useful for the therapeutic application in question, typically in an aqueous buffer. Such an aqueous buffer may comprise an aqueous solvent, a buffer (ii), one or more stabilizing agents (iii), one or more tonicity modifying agents (v), one or more ionic strength modifying agent (iv), an antioxidant (vi), etc. as described hereinabove.

In particular, the container (with its "dry" composition) yields a container as defined hereinabove after reconstitution of the composition with an aqueous solution.

The dry composition within the container is preferably one where the activated Factor VII polypeptide is "stable" as defined herein.

Preparation of a Container Holding the Composition of the Activated Factor VII Polypeptide The closed container of the invention may be prepared in various ways as will be apparent from the following. Typically, the processes for the preparation of the closed container comprise the steps of (i) establishing the activated Factor VII polypeptide in a concentrated form; (ii) if not already present in the suitable container, loading at least a portion of the concentrated Factor VII polypeptide (typically in a solution) into the container so that the container comprises in the range of 2.5-90 mg of the activated Factor VII polypeptide per mL volume of the container; (iii) optionally lyophilizing the concentrated Factor VII polypeptide; and (iv) sealing the container so as to provide the closed container.

aD (i)

Examples of various suitable processes for obtaining a concentrate of the Factor VII polypeptide are described further below.

ad (ii)

If not already present in the suitable container, loading at least a portion of the concentrated Factor VII polypeptide (the concentrate) into the container so that the container comprises in the range of 2.5-90 mg of the activated Factor VII polypeptide per mL volume of the container. Before loading or in connection with the loading, the concentrate may be modified by addition of a buffer (ii), one or more stabilizing agents (iii), one or more tonicity modifying agents (v), one or more ionic strength modifying agent (iv), an antioxidant (vi), etc. as described hereinabove, and the product may be further purified, e.g. by chromatographic processes, mechanical processes (e.g. filtration such as sterile filtration or virus filtra-tion), so as to provide a suitable product for storage in the container. Such a closed container is preferably as defined hereinabove.

ad (iii)

In some important embodiments, the concentrate (possibly after modification as described above under (ii)) may after loading into the container be subjected to freeze-drying so as to obtain a dry product for storage (see also above) which may be reconstituted as described above.

Typically, the container is a vial, carpule, syringe, etc. In one embodiment, the container has at least two compartments (e.g. a carpule) wherein a first compartment holds the activated Factor VII polypeptide. In a variant hereof, the activated Factor VII polypeptide of the first compartment is in lyophilized form, and the second compartment holds an aqueous solvent for said activated Factor VII polypeptide. In another variant hereof, the activated Factor VII polypeptide of the first compartment is in aqueous solution, and the second compartment holds an aqueous solvent for said activated Factor VII polypeptide. In both instances, it is the aim to be able to prepare a ready-to-use composition as defined hereinabove.

ad (iv)

As a final step, the container is closed or sealed so as to provide the closed container by conventional means, e.g. so as to form a vial, carpule, etc. The container may subsequently be labelled and packed.

Anion Exchange Chromatography (AIEC)

In one important variant, the concentrate is obtained with an anion-exchange material and including washing and/or elution with a buffer of a predetermined pH.

According to this aspect of the invention it is certainly possible to obtain a Factor VII polypeptide concentration of up to at least 16 mg/mL, cf. the Experimental section, and it is therefore envisaged that further optimization according to the guidelines given herein will render it possible to provide concentrations suitable for preparing closed containers as defined herein wherein the amount of an activated Factor VII polypeptide is in the range of 2.5-90 mg per mL volume of the container.

In one principal variant, the process for concentration of a drug substance of a Factor VII polypeptide, said drug substance, said process comprises the steps of:

(a) contacting the drug substance with an anion-exchange material under conditions which facilitate binding of a portion of said drug substance to said anion-exchange material (this step is also designated 'load');

(b) washing said anion-exchange material with a washing buffer having a pH in the range of 5.5-7.0, or alternatively in the range of 8.5-9.5 with the presence of 1-7 mM $Ca^{2+}$; and (c) eluting said anion-exchange material with an elution buffer having a pH in the range of 3.0-7.0, and collecting a more concentrated solution of the Factor VII polypeptide as an eluate compared to the load.

A prerequisite for obtaining a concentrated Factor VII polypeptide by AIEC is enhancement of the eluting strength while maintaining an optimal solubility of the Factor VII polypeptide during wash and elution. This is, e.g., obtained by:

(a) holding pH during load at about 5.5-7.0, or alternatively in the range of 8.5-9.5 with the presence of 1-7 mM $Ca^{2+}$.

(b) keeping the ionic strength during wash at 40-250 mM (e.g. NaCl), preferably at 75-100 mM (an ionic strength above 150 mM may cause "bleeding" of the Factor VII polypeptide); and (c) increasing the calcium concentration and/or ionic strength (e.g. NaCl) during elution and/or lowering pH during elution, e.g. from in the range of 5.0-7.0 to in the range of 3.0-4.9, such as in a gradient or as a step.

Although not limited thereto, the AIEC process is particularly feasible for "industrial-scale" (or "large-scale") drug substances of a Factor VII polypeptide. By the term "industrial-scale" is typically meant processes wherein the volume of liquid Factor VII polypeptide compositions is at least 100 L, such as at least 500 L, e.g. at least 1000 L, or at least 5000 L, or where the weight of the compositions is at least 100 kg, such as at least 500 kg, e.g. at least 1000 kg, or at least 5000 kg.

Step (a)—Contacting the Drug Substance with an Anion-Exchange Material

In a first step of the process, the drug substance of the Factor VII polypeptide is contacted with an anion-exchange material. The aim is to facilitate binding of a portion of said drug substance of the Factor VII polypeptide to said anion-exchange material.

By the term "portion" in connection with step (a) is meant at least 30% (i.e. 30-100%) of the mass of the Factor VII polypeptide present in the drug substance of the Factor VII polypeptide. It should be understood that it in most instances is desirable to bind far more than 30% of the mass of the Factor VII polypeptides, e.g. at least 50%, or at least 70%, or a predominant portion. By the term "predominant portion" is meant at least 90% of the mass of the Factor VII polypeptide present in the drug substance of the Factor VII polypeptide. Preferably an even higher portion becomes bound to the anion-exchange material, e.g. at least 95% of the mass, or at least 98% of the mass, or at least 99% of the mass, or even substantially all of the mass of the Factor VII polypeptide present in the drug substance of the Factor VII polypeptide.

The drug substance of the Factor VII polypeptide typically originates from an industrial-scale production process, e.g. a cell culture, a cloned animal (e.g. cows, pigs, sheep, goats, and fish) or insect, or the like, in particular from a cell culture.

The anion-exchange material is preferably a strong anion-exchange material, e.g. an anion-exchange material having quaternary ammonium groups. Commercial examples of such materials are Q-Sepharose Fast Flow, Q-Sepharose High Performance and Mono Q from Amersham Biosciences, POROS HQ 50 from PerSeptive Biosystems and Toyopearl Super Q from Tosoh Biosciences.

The most common arrangement of the anion-exchange material is in the format of a column. Arrangement in a batch container is of course also possible.

The drug substance of the Factor VII polypeptide is typically obtained directly from a preceding purification step, or from a preceding purification step with subsequent adjustment of pH, ionic strength, chelation of divalent metal ions, etc., whatever necessary.

The pH of the drug substance before and upon application to the anion-exchange material play a role for the formation of degradation products such as desGla-Factor VII and heavy chain degradation. Thus, it is preferred that the drug substance is in liquid form and has a pH in the range of 5.5-7.0, e.g. 5.7-6.5, in particular 5.8-6.5 or 5.5-6.2, upon application to the anion-exchange material. For pH values below about 5.5, the tendency towards dimer formation becomes apparent, especially without calcium present. Alternatively, the loading solution has a pH in the range of 8.5-9.5 with the presence of small amounts of calcium, e.g. 1-7 mM.

Typically, the conductivity is in the range of 2-30 mS/cm, such as 5-15 mS/cm. The temperature of the drug substance is typically 0-15° C., such as around 2-10° C.

The temperature of the anion-exchange material with the bound Factor VII polypeptide is typically 0-15° C., such as around 2-10° C., e.g. kept within a specified range by using a cooling jacket and solutions of controlled temperature.

The contacting of the drug substance of the Factor VII polypeptide is typically conducted according to conventional protocols, i.e. the concentration, temperature, ionic strength, etc. of the drug substance may be as usual, and the anion-exchange material may be washed and equilibrated before application as usual.

The load of Factor VII polypeptide is typically in the range of 10-40 g, e.g. 15-30 g, Factor VII polypeptide per liter of matrix (anion-exchange material in wet form), and the drug substance is typically applied at a flow of 3-200 column volumes per hour.

Step (b)—Washing Step

After binding of the drug substance of the Factor VII polypeptide to the anion-exchange materials, a washing step (b) is conducted in order to apply an adequate ionic strength for optimal solubility of the Factor VII polypeptide before start of elution. This step also provides removal of desGla-Factor VII when performed at pH<7.0.

This washing step (b) is preferably effected with a washing buffer having a pH in the range of 5.5-7.0. In some interesting embodiments, the washing buffer has a pH of at the most 6.8, or at the most 6.7, or at the most 6.6, or at the most 6.5, or at the most 6.4. Preferably, the pH is in the range of 5.7-6.5, in particular 5.8-6.5 or 5.5-6.2. In some interesting embodiments, such as loading in the presence of small amounts of calcium up to 7 mM the pH during wash is changed from about pH 9.0 to pH 5.5-7.0.

The washing step (b) is typically conducted at a flow of 3-200 column volumes per hour.

The washing buffer is typically an aqueous solution comprising a buffering agent, typically a buffering agent comprising at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

The washing buffer may also comprise salts, etc., typically a concentration of anions which are insufficient to perform an elution of the Factor VII polypeptide from the column, e.g. corresponding to an ionic strength of 40-250 mM. At pH 6.0, the washing buffer may have a composition of 50-250 mM NaCl, about 10 mM histidine (buffering agent), pH 6.0. In all instances, it is important that the ionic strength of the washing buffer is sufficiently high so as to avoid eventual precipitation of the Factor VII polypeptide but not as high that "bleeding" of the Factor VII polypeptide begins.

It should be understood that the washing step (b) may be conducted by using one, two or several different washing buffers, or by the application of a gradient washing buffer.

Step (c)—Elution Step

After the washing step(s) (c), the anion-exchange material is eluted with an elution buffer, and a concentrated drug substance of the Factor VII polypeptide is collected as an eluate.

A great deal of variability is possible for the elution step (c). If the elution is conducted fairly rapidly, formation of significant amounts of desGla-Factor VII and heavy chain degradation can be suppressed, even if elution is conducted at a pH above 7.0. However, in order to avoid formation of desGla-Factor VII and heavy chain degradation, it is preferred that the elution buffer also has a pH in the range of 3.0-7.0, such as in the range of 4.0-7.0. In some interesting embodiments, the elution buffer has a pH of at the most 6.8, or at the most 6.7, or at the most 6.6, or at the most 6.5, or at the most 6.4.

It appears that the presence of calcium ions in amounts of 5-25 mM reduces degradation, see also the comments hereinafter with regards to ionic strength.

The elution step (b) is typically conducted at a flow of 3-200 column volumes per hour.

The elution can be performed in several ways, such as with an elution buffer comprising divalent cation(s), conduct a competitive elution utilizing a high concentration of certain anions, or to use a pH gradient, or a combination of the before-mentioned.

In one embodiment, elution is effected by means of an elution buffer comprising one or more divalent cation(s). The concentration of the divalent cation(s) is typically at least 5 mM, e.g. at least 10 mM, e.g. at least 15 mM, or even at least 30 mM.

The divalent cation(s) preferably include(s) at least one divalent cation selected from the group consisting of $Ca^{2+}$, $Sr^{2+}$, $Mg^{2+}$, and $Ba^{2+}$. Such divalent cations have a tendency to bind to the Gla-domain of Factor VII polypeptides, and will thereby facilitate liberation of the drug substance of the Factor VII polypeptide from the anion-exchange material. In one preferred embodiment, the divalent cation(s) include(s) $Ca^{2+}$.

The elution buffer typically has a concentration of the divalent cation(s) of at least 5 mM, such as in the range of 5-100 mM, e.g. in the range of 10-50 mM.

In one variant, the elution buffer is a gradient buffer with respect to the divalent cation(s) (e.g. $Ca^{2+}$), e.g. a gradient buffer wherein the initial concentration of the divalent cation(s) (e.g. $Ca^{2+}$) is in the range of 0-20 mM, and the final concentration of the divalent cation(s) (e.g. $Ca^{2+}$) of the gradient buffer is in the range of 15-100 mM.

In another embodiment, the elution step (c) is conducted by competitive elution of the drug substance with one or more anions, e.g. mono-, di- or trivalent anions. Such anions are typically selected from the group consisting of chloride, acetate, malonate, phosphate, carbonate, sulphate, and nitrate; in particular from chloride ($Cl^-$), acetate and malonate.

In one variant, the elution buffer has a concentration of $Cl^-$ in the range of 100-800 mM, e.g. 200-500 mM. Alternatively, the elution buffer is a gradient buffer with respect to $Cl^-$, e.g. a gradient buffer wherein the initial concentration of $Cl^-$ is in the range of 0-300 mM, and the final concentration of $Cl^-$ is in the range of 300-1000 mM.

In a further variant, the elution buffer has a concentration of malonate in the range of 100-800 mM, e.g. 200-500 mM. Alternatively, the elution buffer is a gradient buffer with respect to malonate, e.g. a gradient buffer wherein the initial concentration of malonate is in the range of 0-300 mM, and the final concentration of malonate is in the range of 300-1000 mM.

In a still further variant, the elution buffer has a concentration of acetate in the range of 100-1000 mM, e.g. 400-800 mM. Alternatively, the elution buffer is a gradient buffer with respect to acetate, e.g. a gradient buffer wherein the initial concentration of acetate is in the range of 0-400 mM, and the final concentration of acetate is in the range of 400-1000 mM.

In still another embodiment, the elution buffer is a gradient buffer with respect to pH. In one variant hereof, the initial pH of the gradient buffer is in the range of 5.0-7.0, and the final pH of the gradient buffer is in the range of 3.0-4.9.

With respect to the elution step (c) in general, it is preferred that the ionic strength of the elution buffer is in the range of 100-1000 mM, such as 200-800 mM (e.g NaCl).

Usually, the anion-exchange material is regenerated for the purpose of subsequent use by a sequence of steps.

The present process is particularly useful for obtaining a concentrated drug substance of a Factor VII polypeptide, and if the conditions for the steps (a)-(c) with respect to pH are selected properly, it is even possible to minimize the formation of degradation products of the Factor VII polypeptide structures and thereby increase the overall yield of the process while obtaining a very high concentration of the Factor VII polypeptide.

Thus, a preferred embodiment of the present invention provides a process for the purification of a drug substance of a Factor VII polypeptide, said drug substance comprising an eluate of at least 5 mg/mL the Factor VII polypeptide, said process comprising the steps of:

(a) contacting the drug substance with an anion-exchange material under conditions which facilitate binding of a portion of said drug substance to said anion-exchange material, said drug substance being in liquid form and having a pH in the range of 5.5-7.0, or alternatively in the range of 8.5-9.5 with the presence of 1-7 mM $Ca^{2+}$;

(b) washing said anion-exchange material with a washing buffer having a pH in the range of 5.5-7.0 and an ionic strength in the range of 75-100 mM NaCl; and (c) eluting said anion-exchange material with an elution buffer, the elution buffer having a pH in the range of 2.0-7.0 and comprising a divalent cation such as calcium, the elution buffer having an eluting strength with respect to the divalent cation of 10-30 mM in the presence of 100-300 mM NaCl; using solely the divalent cation for elution the concentration should be at least 50 mM and collecting a concentrated solution of the Factor VII polypeptide as an eluate, the collected purified drug substance comprising a concentration of the FVIIa polypeptide of at least 5 mg/mL with no noteworthy increase in FVIIa polypeptide degradation products.

Hydroxyapatite

In a variant of the above AIEC process, mutatis mutandis, the process for the preparation of a closed container comprising an activated Factor VII polypeptide comprises, mutatis mutandis, the steps of:

(a) contacting a solution comprising a Factor VII polypeptide with a hydroxyapatite material under conditions which facilitate binding of a portion of said Factor VII polypeptide to said hydroxyapatite material (e.g. loaded to about 15 mg/mL gel in the presence of 10 mM calcium);

(b) optionally washing said hydroxyapatite material with a washing buffer (e.g. with first washing buffer of 0.1 M phosphate, pH 6.8, and then 10 mM phosphate, pH 6.8);

(c) eluting said hydroxyapatite material with an elution buffer having a pH in the range of 5.5-7.0, and collecting the eluate of the activated Factor VII polypeptide;

(d) loading at least a portion of the eluate into a container so that the container comprises in the range of 2.5-90 mg of the activated Factor VII polypeptide per mL volume of the container;

(e) optionally lyophilizing the eluate; and (f) sealing the container so as to provide a closed container.

In one variant hereof, it was possible to obtain a bulk concentration of 8 mg/mL.

Ultrafiltration

Ultrafiltration (UF) is a pressure-driven, membrane-based separation technique used to separate extremely small particles and dissolved molecules in fluids. The primary basis for separation is molecular size, although other factors such as molecule shape and charge can also play a role. Molecules larger than the membrane pores will be retained at the surface of the membrane and concentrated during the ultrafiltration process. A pump may be used to generate a continuous flow of solution across the membrane, avoiding build-up of concentrated molecules on the surface of the membrane, and for generation of the necessary pressure to force the water (or liquid) and small molecules, such as buffer components, through the pores of the membrane.

The retention properties of ultrafiltration membranes are expressed as Molecular Weight Cutoff (MWCO). This value refers to the approximate molecular weight (MW) of a dilute globular solute (i.e., a typical protein) which is 90% retained by the membrane. However, a molecule's shape can have a direct effect on its retention by a membrane. For example, linear molecules like DNA may find their way through pores that will retain a globular species of the same molecular weight.

The starting composition to become concentrated by the ultrafiltration process is typically of the same nature as the starting composition of the AIEC process described above. The ion strength is typically in the range of 40-250 mM, and it is desirable to include one or more auxiliary agents such as carbohydrates (e.g. sucrose, mannitol, etc.) as well as buffers, tonicity modifying agents and ionic strength modifying agents as described for the final composition above. The pH of the starting composition is typically in the range of 5.5-7.0, in particular in the range of 5.5-6.5. Precipitation of the Factor VII polypeptide is often observed at pH below 5.5. Alternatively, the pH may be in the range of 9.0-10.0. In most instances, it is preferred to run the process at a low temperature, e.g. in the range of 0-15° C., such as around 2-10° C.

There are three generic applications for ultrafiltration:
1. Concentration. Ultrafiltration is a very efficient process for the concentration of dilute protein (usually over 90% recovery).
2. Desalting and Buffer Exchange (Diafiltration). Ultrafiltration provides a very convenient and efficient way to remove or exchange salts, remove detergents, separate free from bound molecules, remove low molecular weight materials, or rapidly change the ionic or pH environment.
3. Fractionation. Ultrafiltration will not accomplish a sharp separation of two molecules with similar molecular weights. The molecules to be separated should differ by at least one order of magnitude (10×) in size for effective separation.

For a more comprehensive description of ultrafiltration, see e.g.: "Microfiltration and ultrafiltration. Principles and Applications." by Leos 3. Zeman and Andrew L. Zydney. Marcel Dekker, Inc. 270 Madison Avenue, N.Y. (1996).

Accordingly, the container of the invention may also be prepared by a process comprising the steps of:
(a) subjecting a solution comprising a Factor VII polypeptide to ultrafiltration and/or diafiltration so as to obtain a concentrated solution of the Factor VII polypeptide;
(b) loading at least a portion of the concentrated solution into a container so that the container comprises in the range of 2.5-90 mg of the activated Factor VII polypeptide per mL volume of the container;
(c) optionally lyophilizing the solution; and
(d) sealing the container so as to provide a closed container.

Precipitation

Concentration of proteins can be made by precipitating the proteins and then dissolving the precipitate in a smaller volume of the same or a new buffer. The precipitation may be performed by adjusting pH and/or adding a precipitating agent. However, precipitating agents may influence the proteins (denaturation, e.g. organic solvents), and may end up in the precipitate and thereby in the solution after re-dissolving the precipitate. Some precipitating agents are very gentle to the proteins and may even stabilise the proteins and residual precipitating agents may be removed afterwards by e.g. desalting, diafiltration (change of buffer), dialysation or freeze-drying (remove organic solvents like ethanol).

PEG is a highly soluble, uncharged, inflammable polymer with no or very little tendency to denature proteins. Proteins can, therefore, be precipitated by PEG in a safe and gentle way without increasing the conductivity.

A common general process of protein precipitation is salting out at high concentration of a salt, usually ammonium sulfate, $(NH_4)_2SO_4$, because of its high solubility. Ammonium sulfate is also preferred because it does not interact with the proteins and may even have a stabilising effect on the proteins.

The temperature at which the processes are run is typically 0-15° C., such as around 2-10° C.

Accordingly, the container according to the invention may also be prepared by a process comprising the steps of:
(a) combining a saturated solution of ammonium sulphate with a solution comprising a Factor VII polypeptide so as to facilitate precipitation of the Factor VII polypeptide;
(b) redissolving the precipitated Factor VII polypeptide in an aqueous solvent so as to prepare a concentrated solution of the Factor VII polypeptide;
(c) optionally desalting said concentrated solution;
(d) loading at least a portion of the concentrated solution into a container so that the container comprises in the range of 2.5-90 mg of the activated Factor VII polypeptide per mL volume of the container;
(e) optionally lyophilizing the solution; and
(f) sealing the container so as to provide a closed container.

Lyophilization

Lyophilization, or freeze drying, is carried out using a simple principle of physics called sublimation. Sublimation is the transition of a substance from the solid to the vapour state, without first passing through an intermediate liquid phase. To extract water from a frozen solution of e.g. proteins, the process of lyophilization consists of:
1. Freezing the solution so that the water in the solution become ice;
2. Under a vacuum, sublimating the ice directly into water vapour;
3. Drawing off the water vapour;
4. Once the ice is sublimated, the solutes (proteins) are freeze-dried and can be recovered.

For a more comprehensive description of freeze drying, see e.g. "Freeze-Drying/Lyophilization of Pharmaceutical and Biological Products, Second Edition, Series: Drugs and the Pharmaceutical Sciences, Volume: 137, Marcel Dekker, Inc. 270 Madison Avenue, N.Y. (2004).

Accordingly, the container according to the invention may also be prepared by a process comprising the steps of:
(a) lyophilizing a solution comprising a Factor VII polypeptide so as to obtain a composition of the Factor VII polypeptide having a moisture content of not more than about 3%;
(b) redissolving the lyophilized Factor VII polypeptide in an aqueous solvent so as to prepare a concentrated solution of the Factor VII polypeptide;
(c) optionally desalting said concentrated solution;

(d) loading at least a portion of the concentrated solution into a container so that the container comprises in the range of 2.5-90 mg of the activated Factor VII polypeptide per mL volume of the container;

(e) optionally lyophilizing the solution; and (f) sealing the container so as to provide a closed container.

Use of the Container Holding the Composition of the Activated Factor VII Polypeptide The pharmaceutical products represented by the closed containers are particularly useful for therapeutic applications wherein a fairly large amount of the activated Factor VII polypeptide can be provided with one container. Thus, the present invention in particular provides pharmaceutical products as defined herein for use as a medicament, more particular for use as a medicament for treating a Factor VII-responsive syndrome, such as, e.g., bleeding disorders, including those caused by clotting Factor deficiencies (e.g., e.g. haemophilia A, haemophilia B, coagulation Factor XI deficiency, coagulation Factor VII deficiency); by thrombocytopenia or von Willebrand's disease, or by clotting Factor inhibitors, and intra cerebral haemorrhage, or excessive bleeding from any cause. The preparations may also be administered to patients in association with surgery or other trauma or to patients receiving anticoagulant therapy, in particular where such conditions require a dose of more than 40 µg/kg body weight.

The term "treatment" is defined as the management and care of a subject, e.g. a mammal, in particular a human, for the purpose of combating the disease, condition, or disorder and includes the administration of a Factor VII polypeptide to prevent the onset of the symptoms or complications, or alleviating the symptoms or complications, or eliminating the disease, condition, or disorder. Pharmaceutical compositions according to the present invention containing a Factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

In important embodiments, the pharmaceutical composition is adapted to subcutaneous, intramuscular or intravenous injection according to methods known in the art.

A Kit and a Method for Using the Kit

In view of the above, the present invention also provides a kit including the novel container defined above. Thus, the present invention provides a kit comprising (i) a closed first container containing a solid pharmaceutical composition of an activated Factor VII polypeptide and (ii) a second container containing a liquid, aqueous solvent for said solid pharmaceutical composition, wherein the first container holds a composition comprising in the range of 2.5-90 mg of the activated Factor VII polypeptide per mL volume of the first container.

The first container, the composition and the activated Factor VII polypeptide, are generally and specifically as defined above for the closed container.

In one embodiment, the first container and the second container is arranged as a carpule where one compartment corresponds to the first container and another, adjacent compartment corresponds to the second container.

The present invention also provides the medical use of the kit, a method for the preparation of a ready-to-use liquid, aqueous pharmaceutical composition of an activated Factor VII polypeptide from a kit as defined above, the method comprising mixing the solid pharmaceutical composition of the first container with at least a fraction of the liquid, aqueous solvent of the second container so as to form the ready-to-use liquid, aqueous pharmaceutical composition of an activated Factor VII polypeptide.

In one variant of the method, essentially all of the liquid, aqueous solvent of the second container is mixed with the solid pharmaceutical composition of the first container.

Activated Factor VII Polypeptide

As used herein, the terms "FVII", "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "wild type human FVIIa" is a polypeptide having the amino acid sequence disclosed in U.S. Pat. No. 4,784,950.

As used herein, "Factor VII-related polypeptides" encompasses polypeptides, including variants, in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, L305V-FVII, L305V/M306D/D309S-FVII, L305T-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVI1, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/

L305V/V158D/M298Q-FVII, F374Y/L305V/V158D/ S314E-FVII, F374Y/L305V/E296V/M298Q-FVII, F374Y/ L305V/E296V/V158T-FVII, F374Y/L305V/E296V/S314E-FVII, F374Y/L305V/M298Q/V158T-FVII, F374Y/L305V/ M298Q/S314E-FVII, F374Y/L305V/V158T/S314E-FVII, F374Y/K337A/S314E/V158T-FVII, F374Y/K337A/S314E/ M298Q-FVII, F374Y/K337A/S314E/E296V-FVII, F374Y/ K337A/S314E/V158D-FVII, F374Y/K337A/V158T/ M298Q-FVII, F374Y/K337A/V158T/E296V-FVII, F374Y/ K337A/M298Q/E296V-FVII, F374Y/K337A/M298Q/ V158D-FVII, F374Y/K337A/E296V/V158D-FVII, F374Y/ V158D/S314E/M298Q-FVII, F374Y/V158D/S314E/ E296V-FVII, F374Y/V158D/M298Q/E296V-FVII, F374Y/ V158T/S314E/E296V-FVII, F374Y/V158T/S314E/ M298Q-FVII, F374Y/V158T/M298Q/E296V-FVII, F374Y/ E296V/S314E/M298Q-FVII, F374Y/L305V/M298Q/ K337A/S314E-FVII, F374Y/L305V/E296V/K337A/ S314E-FVII, F374Y/E296V/M298Q/K337A/S314E-FVII, F374Y/L305V/E296V/M298Q/K337A-FVII, F374Y/ L305V/E296V/M298Q/S314E-FVII, F374Y/V158D/ E296V/M298Q/K337A-FVII, F374Y/V158D/E296V/ M298Q/S314E-FVII, F374Y/L305V/V158D/K337A/ S314E-FVII, F374Y/V158D/M298Q/K337A/S314E-FVII, F374Y/V158D/E296V/K337A/S314E-FVII, F374Y/ L305V/V158D/E296V/M298Q-FVII, F374Y/L305V/ V158D/M298Q/K337A-FVII, F374Y/L305V/V158D/ E296V/K337A-FVII, F374Y/L305V/V158D/M298Q/ S314E-FVII, F374Y/L305V/V158D/E296V/S314E-FVII, F374Y/V158T/E296V/M298Q/K337A-FVII, F374Y/ V158T/E296V/M298Q/S314E-FVII, F374Y/L305V/ V158T/K337A/S314E-FVII, F374Y/V158T/M298Q/ K337A/S314E-FVII, F374Y/V158T/E296V/K337A/ S314E-FVII, F374Y/L305V/V158T/E296V/M298Q-FVII, F374Y/L305V/V158T/M298Q/K337A-FVII, F374Y/ L305V/V158T/E296V/K337A-FVII, F374Y/L305V/ V158T/M298Q/S314E-FVII, F374Y/L305V/V158T/ E296V/S314E-FVII, F374Y/E296V/M298Q/K337A/ V158T/S314E-FVII, F374Y/V158D/E296V/M298Q/ K337A/S314E-FVII, F374Y/L305V/V158D/E296V/ M298Q/S314E-FVII, F374Y/L305V/E296V/M298Q/ V158T/S314E-FVII, F374Y/L305V/E296V/M298Q/ K337A/V158T-FVII, F374Y/L305V/E296V/K337A/ V158T/S314E-FVII, F374Y/L305V/M298Q/K337A/ V158T/S314E-FVII, F374Y/L305V/V158D/E296V/ M298Q/K337A-FVII, F374Y/L305V/V158D/E296V/ K337A/S314E-FVII, F374Y/L305V/V158D/M298Q/ K337A/S314E-FVII, F374Y/L305V/E296V/M298Q/ K337A/V158T/S314E-FVII, F374Y/L305V/V158D/ E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/ A292T-FVII, G291N-FVII, R315N/V317T-FVII, K143N/ N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

For purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) Measuring the ability of the Factor VII polypeptide to produce activated Factor X (Factor Xa) in a system comprising TF embedded in a lipid membrane and Factor X. (Persson et al., J. Biol. Chem. 272:19919-19924, 1997);

(ii) Measuring Factor X hydrolysis in an aqueous system ("In Vitro Proteolysis Assay" (Assay 2), below);

(iii) Measuring the physical binding of the Factor VII polypeptide to TF using an instrument based on surface plasmon resonance (Persson, FEBS Letts. 413:359-363, 1997);

(iv) Measuring hydrolysis of a synthetic substrate by the Factor VII polypeptide ("In Vitro Hydrolysis Assay" (Assay 1), below); and (v) Measuring generation of thrombin in a TF-independent in vitro system ("Thrombin generation Assay" (Assay 3), below).

In some embodiments, the Factor VII polypeptide is human Factor VIIa, preferably recombinantly made human Factor VIIa.

In other embodiments, the Factor VII polypeptide is a Factor VII sequence variant.

In some embodiments, the Factor VII polypeptide has a glycosylation different from wild-type human Factor VII.

In various embodiments, e.g. those where the Factor VII polypeptide is a Factor VII-related polypeptide or a Factor VII sequence variant, the ratio between the activity of the Factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" (Assay 2) as described in the present specification.

In some embodiments, the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see Assay 1 below); in other embodiments, the ratio is at least about 2.0; in further embodiments, the ratio is at least about 4.0.

The compositions according to the present invention are useful as stable and preferably ready-to-use compositions of Factor VII polypeptides. The compositions are typically stable for at least six months, and preferably up to 36 months; when stored at temperatures ranging from 2° C. to 8° C.

The term "Stable" is intended to denote that (i) after storage for 6 months at 2° C. to 8° C. the composition retains at least 50% of its initial biological activity as measured by a one-stage clot assay (Assay 4), or (ii) after storage for 6 months at 2° C. to 8° C., the increase in content of heavy chain degradation products is at the most 40% (w/w) of the initial content of Factor VII polypeptide.

The term "initial content" relates to the amount of Factor VII polypeptide added to a composition upon preparation of the composition.

Preferably, the stable composition retains at least 70%, such as at least 80%, or at least 85%, or at least 90%, or at least 95%, of its initial biological activity after storage for 6 months at 2 to 8° C.

Preferably, in various embodiments the increase in content of heavy chain degradation products in stable compositions is not more than about 30% (w/w), not more than about 25% (w/w), not more than about 20% (w/w), not more than about 15% (w/w), not more than about 10% (w/w), not more than about 5% (w/w), or not more than about 3% (w/w), of the initial content of Factor VII polypeptide.

In a preferred embodiment, the composition (i) after storage for 6 months at 20° C. to 28° C. the composition retains at least 50% of its initial biological activity as measured by a one-stage clot assay (Assay 4), or (ii) after storage for 6 months at 20° C. to 28° C., the increase in content of heavy chain degradation products is at the most 40% (w/w) of the initial content of Factor VII polypeptide. In a more preferred embodiment, the composition (i) after storage for 6 months at 37° C. to 43° C. the composition retains at least 50% of its initial biological activity as measured by a one-stage clot assay (Assay 4), or (ii) after storage for 6 months at 37° C. to 43° C., the increase in content of heavy chain degradation products is at the most 40% (w/w) of the initial content of Factor VII polypeptide.

Preparation and Purification of Factor VII Polypeptides

Human purified Factor VIIa suitable for use in the present invention is preferably made by DNA recombinant technology, e.g. as described by Hagen et al., Proc. Natl. Acad. Sci. USA 83: 2412-2416, 1986, or as described in European Patent No. 0 200 421 (ZymoGenetics, Inc.). Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation Factors. An even further purified Factor VII preparation may be obtained by including an additional gel filtration as the final purification step. Factor VII is then converted into activated Factor VIIa by known means, e.g. by several different plasma proteins, such as Factor XIIa, IX a or Xa. Alternatively, as described by Bjoern et al. (Research Disclosure, 269 September 1986, pp. 564-565), Factor VII may be completely activated by passing it through an ion-exchange chromatography column, such as Mono Q® (Pharmacia fine Chemicals) or the like, or by autoactivation in solution.

Factor VII-related polypeptides may be produced by modification of wild-type Factor VII or by recombinant technology. Factor VII-related polypeptides with altered amino acid sequence when compared to wild-type Factor VII may be produced by modifying the nucleic acid sequence encoding wild-type Factor VII either by altering the amino acid codons or by removal of some of the amino acid codons in the nucleic acid encoding the natural Factor VII by known means, e.g. by site-specific mutagenesis.

It will be apparent to those skilled in the art that substitutions can be made outside the regions critical to the function of the Factor VIIa molecule and still result in an active polypeptide. Amino acid residues essential to the activity of the Factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super-coiled, double-stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemi-methylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any process known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any process known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than 10% by weight, more preferably less than 5% and most preferably less than 1%, of non-Factor VII polypeptides derived from the host cell.

If not completely activated in the preparation of the concentrate of the Factor VII polypeptide, the Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution.

EXPERIMENTALS

General Methods

Assays Suitable for Determining Biological Activity of Factor VII Polypeptides

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=($A$405 nm Factor VII polypeptide)/
($A$405 nm Factor VIIa wild-type).

Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 μL 50 mM HEPES, pH 7.4, containing 0.1 M NaCl, 5 mM $CaCl_2$ and 1 mg/mL bovine serum albumin, are incubated for 15 min. Factor X cleavage is then stopped by the addition of 50 μL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=($A$405 nm Factor VII polypeptide)/
($A$405 nm Factor VIIa wild-type).

Based thereon, a Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

Thrombin Generation Assay (Assay 3)

The ability of a Factor VII polypeptides to generate thrombin can be measured in an assay (Assay 3) comprising all relevant coagulation Factors and inhibitors at physiological concentrations (minus Factor VIII when mimicking hemophilia A conditions) and activated platelets (as described on p. 543 in Monroe et al. (1997) Brit. J. Haematol. 99, 542-547 which is hereby incorporated as reference).

One-Stage Coagulation Assay (Clot Assay) (Assay 4)

Factor VII polypeptides may also be assayed for specific activities ("clot activity") by using a a one-stage coagulation assay (Assay 4). For this purpose, the sample to be tested is diluted in 50 mM PIPES-buffer (pH 7.2), 1% BSA and 40 μl is incubated with 40 μl of Factor VII deficient plasma and 80 μl of Innovine (Dade-Behring; cat. no. B4212-50). Coagulation times (clotting times) are measured and compared to a standard curve using a reference standard in a parallel line assay.

Heavy Chain Degradation and Oxidized Forms (Assay 5)

In the below working examples the content of heavy chain degradation products and the content of oxidized forms are determined by reverse-phase HPLC(RP-HPLC) as described in the following:

Reverse phase HPLC was run on a proprietary 4.5×250 mm butyl-bonded silica column with a particle size of 5 g/m and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13) % B in 30 minutes. X was adjusted so that FVIIa elutes with a retention time of approximately 26 minutes. Flow rate: 1.0 mL/min. Detection: 214 nm. Load: 25 μg FVIIa.

Content of Aggregates (Assay 6)

In the below working examples the content of aggregates is determined by non-denaturing size exclusion HPLC (SE-HPLC) as described in the following:

Non-denaturing size exclusion chromatography was run on a Waters Protein Pak 300 SW column, 7.5×300 mm using 0.2 M ammoniumsulfat, 5% 2-propanol pH 7.0 as mobile phase. Flow rate: 0.5 mL/min. Detection: 215 nm. Load: 25 μl FVIIa.

Determination of Content of desGla-Factor VII Polypeptide Structures

The content of desGla-Factor VII polypeptide structures relative to the full length Factor VII polypeptide structures is determined by SDS-PAGE. 150 μl of sample is added 50 μl of sample buffer (non-reducing, NuPAGE) and boiled for 5 mins. A 10 μl sample is loaded onto a 12% BisTris NuPAGE Gel (Invitrogen). The gel is run at 200 Volts, 120 mA for 55 mins. The gel is stained using coomassie brilliant blue solution, destained and dried. The relative desGla-Factor VII polypeptide content is calculated as the area of the desGla-Factor VII polypeptide band divided by the areas of the Factor VII polypeptide band at approx. 50 kDa and desGla-Factor VII polypeptide band at approx. 45 kDa.

Alternatively, the content of desGla-Factor VII polypeptide structures may be determined by anion exchange HPLC. The method separates Gla-domain-less Factor VII polypeptides from intact Factor VII polypeptides. The content of Gla-domain-less Factor VII polypeptides is expressed in % of the Factor VII polypeptide related peak area. As analytical column is used a DNAPac PA-100, 250×4 mm (Dionex Corp.). The column is eluted with a linear gradient from 0-0.5 M ammonium acetate at pH 9.0 over 30 minutes at a flow of 1.0 mL/min. The absorbance at 280 nm of the effluent is monitored.

Examples

The following examples illustrate the invention. These examples are included for illustrative purposes only and are not intended in any way to limit the scope of the invention claimed.

Example 1

Concentration is performed on an anion exchange chromatography (AIEC) column (1.6 cm inner diameter×7.5 cm length=15 mL column volume (CV)) packed with Amersham Q-sepharose Fast Flow media, equilibrated with a solution containing 50 mM NaCl, 20 mM tri-sodium-citrate, pH 7.0. The load is 12 CVs of a solution containing 1.4 mg/mL FVIIa, followed by a 7 CV wash using 50 mM NaCl, 20 mM tri-sodium-citrate, pH 7.0. The elution is performed using a step gradient to 50 mM NaCl, 20 mM tri-sodium-citrate, pH 4.2. The entire purification is carried out at a flow-rate of 40 CV/h and a temperature of 5° C. The product peak elutes after approximately 3.3 CV and the eluate is adjusted to pH 6.0/ NaOH. The eluate concentration is 3.3 mg/mL measured by RP-HPLC.

Example 2

Concentration is performed on an AIEC column (same size as previous) packed with Amersham Q-sepharose Fast Flow media, equilibrated with a solution containing 10 mM EDTA, 10 mM Histidine, pH 6.0. The load is 12 CVs of a solution containing 1.4 mg/mL FVIIa, followed by a 5 CV wash1 using 175 mM NaCl, 10 mM Histidine, pH 6.0 and a 5 CV wash 2 using 50 mM NaCl, 10 mM Histidine, pH 6.0. The elution is performed using a step gradient to 30 mM $CaCl_2$, 50 mM NaCl, buffered at pH 6.0 by 10 mM Histidine. The entire purification is carried out at a flow-rate of 40 CV/h and a temperature of 5° C. The product peak elutes after approximately 1.9 CV. The eluate concentration is 6.1 mg/mL measured by RP-HPLC.

Example 3

Concentration is performed on an AIEC column (same size as previous) packed with Amersham Q-sepharose Fast Flow media, equilibrated with a solution containing 10 mM EDTA, 10 mM Histidine, pH 6.0. The load is 12 CVs of a solution containing 1.4 mg/mL FVIIa, followed by a 5 CV wash using 50 mM NaCl, 10 mM Histidine, pH 6.0. The elution is performed using a step gradient to 30 mM $CaCl_2$, 50 mM NaCl, buffered at pH 6.0 by 10 mM Histidine. The entire purification is carried out at a flow-rate of 40 CV/h and a temperature of 5° C. The product peak elutes after approximately 1.9 CV. The eluate concentration is 5.4 mg/mL measured by RP-HPLC.

Example 4

Concentration is performed on an AIEC column (same size as previous) packed with Amersham Q-sepharose Fast Flow media, equilibrated with a solution containing 10 mM EDTA, 10 mM Histidine, pH 6.0. The load is 12 CVs of a solution containing 1.4 mg/mL FVIIa, followed by a 5 CV wash using 50 mM NaCl, 10 mM Histidine, pH 6.0. The elution is performed using a step gradient to 10 mM $CaCl_2$, 50 mM NaCl, buffered at pH 6.0 by 10 mM Histidine. The entire purification is carried out at a flow-rate of 40 CV/h and a temperature of 5° C. The product peak elutes after approximately 2.2 CV. The eluate concentration is 4.6 mg/mL measured by RP-HPLC.

Example 5

Concentration is performed on an AIEC column (same size as previous) packed with Amersham Q-sepharose Fast Flow media, equilibrated with a solution containing 10 mM EDTA, 10 mM Histidine, pH 6.0. The load is 12 CVs of a solution containing 1.4 mg/mL FVIIa, followed by a 5 CV wash using 50 mM NaCl, 10 mM Histidine, pH 6.0. The elution is performed using a step gradient to 10 mM $CaCl_2$, 100 mM NaCl, buffered at pH 6.0 by 10 mM Histidine. The entire purification is carried out at a flow-rate of 40 CV/h and a temperature of 5° C. The product peak elutes after approximately 1.4 CV. The eluate concentration is 9.1 mg/mL measured by RP-HPLC.

Example 6

Concentration is performed on an AIEC column (same size as previous) packed with Amersham Q-sepharose Fast Flow media, equilibrated with a solution containing 10 mM EDTA, 10 mM Histidine, pH 6.0. The load is 12 CVs of a solution containing 1.4 mg/mL FVIIa, followed by a 5 CV wash using 50 mM NaCl, 10 mM Histidine, pH 6.0. The elution is performed using a step gradient to 10 mM $CaCl_2$, 200 mM NaCl, buffered at pH 6.0 by 10 mM Histidine. The entire purification is carried out at a flow-rate of 40 CV/h and a temperature of 5° C. The product peak elutes after approximately 1.4 CV. The eluate concentration is 10.0 mg/mL measured by RP-HPLC.

Example 7

Concentration is performed on an AIEC column (same size as previous) packed with Applied Biosystems POROS 50 HQ media, equilibrated with a solution containing 10 mM EDTA, 10 mM Histidine, pH 6.0. The load is 11 CVs of a solution containing 1.4 mg/mL FVIIa, followed by a 5 CV wash using 50 mM NaCl, 10 mM Histidine, pH 6.0. The elution is performed using a step gradient to 10 mM $CaCl_2$, 100 mM NaCl, buffered at pH 6.0 by 10 mM Histidine. The equilibration, load and wash are carried out at a flow-rate of 80 CV/h and a temperature of 5° C. and the elution is run at 40 CV/h. The product peak elutes after approximately 1.5 CV. The eluate concentration is 6.6 mg/mL measured by RP-HPLC.

Example 8

Concentration is performed on an AIEC column (same size as previous) packed with Applied Biosystems POROS 50 HQ media, equilibrated with a solution containing 10 mM EDTA, 10 mM Histidine, pH 6.0. The load is 11 CVs of a solution containing 1.4 mg/mL FVIIa, followed by a 5 CV wash using 50 mM NaCl, 10 mM Histidine, pH 6.0. The elution is performed using a step gradient to 10 mM $CaCl_2$, 200 mM NaCl, buffered at pH 6.0 by 10 mM Histidine. The equilibration, load and wash are carried out at a flow-rate of 80 CV/h and a temperature of 5° C. and the elution is run at 40 CV/h. The product peak elutes after approximately 1.4 CV. The eluate concentration is 16.0 mg/mL measured by RP-HPLC.

Example 9

Concentration is performed on an AIEC column (same size as previous) packed with Applied Biosystems POROS 50 HQ media, equilibrated with a solution containing 10 mM EDTA, 10 mM Histidine, pH 6.0. The load is 11 CVs of a solution containing 1.4 mg/mL FVIIa, followed by a 5 CV wash using 50 mM NaCl, 10 mM Histidine, pH 6.0. The elution is performed using a linear gradient over 5 CV to 30 mM $CaCl_2$, 100 mM NaCl, buffered at pH 6.0 by 10 mM Histidine. The equilibration, load and wash are carried out at a flow-rate of 80 CV/h and a temperature of 5° C. and the elution is run at 40 CV/h. The product peak elutes after approximately 3.0 CV. The eluate concentration is 8.2 mg/mL measured by RP-HPLC.

Example 10

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 5 CV wash using 50 mM NaCl, 10 mM Histidine, pH 6.0. The elution is performed using a linear gradient over 5 CV to 30 mM $CaCl_2$, 100 mM NaCl, buffered at pH 6.0 by 10 mM Histidine. The load and wash are carried out at a flow-rate of 120 CV/h and a temperature of 5° C. and the elution is run at 40 CV/h. The product peak elutes after approximately 2.9 CV. The eluate concentration is 7.8 mg/mL measured by RP-HPLC.

Example 11

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 5 CV wash1 using 50 mM NaCl, 10 mM Histidine, pH 6.0 and a 2 CV wash2 using 10 mM Histidine, pH 6.0. The elution is performed using a linear gradient over 5 CV to 50 mM $CaCl_2$, buffered at pH 6.0 by 10 mM Histidine. The load and wash are carried out at a flow-rate of 120 CV/h and a temperature of 5° C. and the elution is run at 40 CV/h. The product peak elutes after approximately 3.2 CV. The eluate concentration is 7.3 mg/mL measured by RP-HPLC.

Example 12

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 5 CV wash1 using 5 mM $CaCl_2$, 10 mM Histidine, pH 6.0 and a 2 CV wash2 using 10 mM Histidine, pH 6.0. The elution is performed using a linear gradient over 5 CV to 50 mM $CaCl_2$, buffered at pH 6.0 by 10 mM Histidine. The load and wash are carried out at a flow-rate of 120 CV/h and a temperature of 5° C. and the elution is run at 40 CV/h. The product peak elutes after approximately 3.2 CV. The eluate concentration is 6.4 mg/mL measured by RP-HPLC.

Example 13

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 5 CV wash1 using 5 mM $CaCl_2$, 10 mM Histidine, pH 6.0 and a 2 CV wash2 using 10 mM Histidine, pH 6.0. The elution is performed using a step gradient to 50 mM $CaCl_2$, buffered at pH 6.0 by 10 mM Histidine. The load and wash are carried out at a flow-rate of 120 CV/h and a temperature of 5° C. and the elution is run at 40 CV/h. The product peak elutes after approximately 1.3 CV. The eluate concentration is 16.0 mg/mL measured by RP-HPLC.

Example 14

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 6 CV wash using 5 mM $CaCl_2$, 10 mM Histidine, pH 6.0. The elution is performed using a linear gradient over 5 CV to 50 mM $CaCl_2$, buffered at pH 6.0 by 10 mM Histidine. The load and wash are carried out at a flow-rate of 120 CV/h and a temperature of 5° C. and the elution is run at 40 CV/h. The product peak elutes after approximately 2.8 CV. The eluate concentration is 7.8 mg/mL measured by RP-HPLC.

Example 15

Concentration is performed on an AIEC column (same size as previous) packed with Applied Biosystems POROS 50 HQ media, equilibrated with a solution containing 10 mM glycylglycine, 5 mM $CaCl_2$, pH 9.0. The load is 22 CVs of a solution containing 0.7 mg/mL FVIIa and 5 mM $CaCl_2$, followed by a 6 CV wash using 5 mM $CaCl_2$, 10 mM Histidine, pH 6.0. The elution is performed using a linear gradient over 2 CV to 50 mM $CaCl_2$, buffered at pH 6.0 by 10 mM Histidine. The load and wash are carried out at a flow-rate of 120 CV/h and a temperature of 5° C. and the elution is run at 40 CV/h. The product peak elutes after approximately 2.0 CV. The eluate concentration is 9.0 mg/mL measured by RP-HPLC.

Run conditions and analytical data on eluate from above-described Examples 1-15 are shown in Table 1 (below).

TABLE 1

| | | | | | | yield (%/%) | | heavy chain | | | |
| Ex. | media | load pH | Wash | elution | conc mg/mL | eluate/ total | GD-FVIIa % | degradation % | oxidation % | polymers % | dimer/-oligomer % |
| --- | --- | --- | --- | --- | --- | --- | --- | --- | --- | --- | --- |
| 1 | Q FF | 7.0 | 50 mM NaCl, 20 mM tri-Na-citrate pH 7.0 | Step gradient pH 7.0 → 4.2 | 3.3 | 75/81 | NA | 8.7 | 2.2 | 0.07 | 3.6 |

TABLE 1-continued

Run conditions and analytical data on eluate

| Ex. | media | load pH | Wash | elution | conc mg/mL | yield (%/%) eluate/total | GD-FVIIa % | heavy chain degradation % | oxidation % | polymers % | dimer/oligomer % |
|---|---|---|---|---|---|---|---|---|---|---|---|
| 2 | Q FF | 6.0 | 175 mM NaCl, 10 mM histidine pH 6.0 | Step gradient to 30 mM CaCl$_2$, 50 mM NaCl | 6.1 | 52/86 | NA | 11.0 | 2.2 | 0.02 | 2.4 |
| 3 | Q FF | 6.0 | 50 mM NaCl, 10 mM histidine pH 6.0 | Step gradient to 30 mM CaCl$_2$, 50 mM NaCl | 5.4 | 79/85 | NA | 10.8 | 2.5 | 0.03 | 1.8 |
| 4 | Q FF | 6.0 | 50 mM NaCl, 10 mM histidine pH 6.0 | Step gradient to 10 mM CaCl$_2$, 50 mM NaCl | 4.6 | 72/82 | NA | 10.2 | 1.5 | 0.05 | 1.1 |
| 5 | Q FF | 6.0 | 50 mM NaCl, 10 mM histidine pH 6.0 | Step gradient to 10 mM CaCl$_2$, 100 mM NaCl | 9.1 | 77/89 | NA | 11.1 | 1.9 | 0.01 | 3.0 |
| 6 | Q FF | 6.0 | 50 mM NaCl, 10 mM histidine pH 6.0 | Step gradient to 10 mM CaCl$_2$, 200 mM NaCl | 10.0 | 85/94 | NA | 9.8 | 2.0 | 0 | 2.9 |
| 7 | POROS | 6.0 | 50 mM NaCl, 10 mM histidine pH 6.0 | Step gradient to 10 mM CaCl$_2$, 100 mM NaCl | 6.6 | 56/68 | NA | 11.5 | 2.1 | NA | NA |
| 8 | POROS | 6.0 | 50 mM NaCl, 10 mM histidine pH 6.0 | Step gradient to 10 mM CaCl$_2$, 200 mM NaCl | 16.0 | 81/86 | <1.0 | 11.5 | 1.8 | NA | NA |
| 9 | POROS | 6.0 | 50 mM NaCl, 10 mM histidine pH 6.0 | Linear gradient 5 CV to 30 mM CaCl$_2$, 100 mM NaCl | 8.2 | 74/84- | <1.0 | 7.2 | 1.8 | 0.07 | 2.7 |
| 10 | POROS | 9.0/5 mM Ca$^{2+}$ | 50 mM NaCl, 10 mM histidine pH 6.0 | Linear gradient 5 CV to 30 mM CaCl$_2$, 100 mM NaCl | 7.8 | 66/79 | 1.2 | 10.0 | 1.9 | 0.02 | 1.1 |
| 11 | POROS | 9.0/5 mM Ca$^{2+}$ | 50 mM NaCl, 10 mM histidine pH 6.0 | Linear gradient 5 CV to 50 mM CaCl$_2$ | 7.3 | 63/75 | NA | 9.7 | 1.5 | 0.04 | 2.2 |
| 12 | POROS | 9.0/5 mM Ca$^{2+}$ | 5 mM CaCl$_2$, 10 mM histidine pH 6.0 | Linear gradient 5 CV to 50 mM CaCl$_2$ | 6.4 | 52/61 | NA | 10.1 | 1.8 | 0.01 | 1.3 |
| 13 | POROS | 9.0/5 mM Ca$^2$ | 10 mM histidine pH 6.0 | Step gradient to 50 mM CaCl$_2$ | 16.0 | 85/91 | NA | 9.6 | 1.4 | 0.06 | 1.6 |
| 14 | POROS | 9.0/5 mM Ca$^{2+}$ | 5 mM CaCl$_2$, 10 mM histidine pH 6.0 | Linear gradient 5 CV to 50 mM CaCl$_2$ | 7.8 | 74/88 | NA | 8.5 | <1.0 | 0.03 | 1.7 |
| 15 | POROS | 9.0/5 mM Ca$^{2+}$ | 5 mM CaCl$_2$, 10 mM histidine pH 6.0 | Linear gradient 2 CV to 50 mM CaCl$_2$ | 9.0 | 82/90 | NA | 10.5 | 2.0 | 0.04 | 1.7 |

Precipitation

Example 16

To 250 mL of rFVIIa bulk solution, with a concentration of 1.2 mg rFVIIa/mL in a buffer containing 50 mM NaCl, 10 mM CaCl$_2$, 10 mM Glycyl-glycin, pH 6.4, was added 112.5 g of ammonium sulfate (65% saturation). After 15 minutes with gentle stirring, the solution was centrifuged for 1 hour at approximately 4000 G (4500 rpm) in a Heraus Sorvall Labofuge at 4° C. The precipitate was dissolved in 30 mL of a buffer containing 100 mM NaCl, 10 mM CaCl$_2$, 10 mM histidine, pH 6.0 and filtered through 0.2 μm filter. The concentration of rFVIIa in the re-dissolved precipitate was measured to 8.3 mg/mL by OD$_{280}$ and to 7.8 mg/mL by RP-HPLC. The level of heavy chain degradation was 8.3% before precipitation and 8.5% after precipitation. There was a slight drop in GD-FVIIa and a slight increase in oligomers/dimers at the precipitation (Table 2).

TABLE 2

Results of analyses before and after precipitation with ammonium sulfate.

| Sample | Concentration of rVIIa, mg/mL | Heavy chain degradation, % | Oxidation % | GD-FVIIa, % | Polymers, % | Oligomers/ dimers, % |
|---|---|---|---|---|---|---|
| Bulk before precipitation | 1.2 | 8.3 | 3.9 | 3.9 | 0.05 | 1.0 |
| Bulk after precipitation | 7.8 | 8.5 | 2.0 | 2.0 | 0.04 | 1.6 |

Ultrafiltration

Example 17

A Labscale TFF System (Millipore, equipped with a Pellicon XL Filter Device with Biomax 30 kD membrane (Millipore no. PXB030A50) was used for ultrafiltration (UF) of 247 mL rFVIIa bulk. The UF was performed at 2-8° C. with a flow across the membrane of 20-30 mL/minute, and an inlet pressure of 1-1.5 bar. Before UF, the bulk contained 1.2 mg/mL of rFVIIa in a buffer with 50 mM NaCl, 10 mM $CaCl_2$, 10 mM Glycyl-glycin, pH 6.05. The bulk was added citrate until a final concentration of 20 mM and then concentrated on the UF-system until a volume of 80 mL. A diafiltration was performed at constant volume, using 400 mL of a buffer containing 200 mM NaCl, 1 mM citrate, pH 6.0. After diafiltration, the solution was concentrated further until a volume of 40 mL. The concentration of rFVIIa after diafiltration/concentration was 6.3 mg/mL as measured by both $OD_{280}$ and by SEC-HPLC. No significant change was seen in the levels of heavy chain degradation, GD-FVIIa or polymers, but the level of oligomers/dimers increased slightly (Table 3)

TABLE 3

Results of analyses before and after diafiltration/concentration by UF.

| Sample | Heavy chain degradation % | GD-FVIIa, % | Oxidation % | Polymers, % | Oligomers/ dimers, % | Concentration of rVIIa, mg/mL |
|---|---|---|---|---|---|---|
| Bulk before ultra filtration | 9.5 | 4.6 | 2.1 | 0.03 | 1.0 | 1.2 |
| Bulk after ultra filtration | 9.6 | 4.8 | 2.0 | 0.02 | 1.6 | 6.3 |

Example 20

The same UF-system as in example 17 was used for concentration of rFVIIa bulk without diafiltration. Before concentration, the volume of the rFVIIa bulk was 189 mL and the concentration of rFVIIa was 1.1 mg/mL in a buffer with 50 mM NaCl, 10 mM $CaCl_2$, 10 mM Glycyl-glycin, pH 6.05. $CaCl_2$ was added, so that the final concentration of $CaCl_2$ was enhanced to a total of 30 mM. After concentration by UF, the volume of the solution was 23 mL and the concentration of rFVIIa was 7.1 mg/mL as measured by $OD_{280}$ and 7.6 as measured by SEC-HPLC. No significant change was seen in the levels of heavy chain degradation, GD-FVIIa, polymers or oligomers/dimers from before UF to after UF (Table 4).

TABLE 4

Results of analyses before and after addition of $CaCl_2$ and concentration by UF.

| Sample | Heavy chain degradation, % | GD-FVIIa, % | Oxidation % | Polymers, % | Oligomers/ dimers, % | Concentration of rVIIa, mg/mL |
|---|---|---|---|---|---|---|
| Bulk before ultra filtration | 9.5 | 4.3 | 2.2 | 0.06 | 0.8 | 1.1 |
| Bulk after ultra filtration | 9.6 | 4.3 | 2.3 | 0.05 | 0.8 | 7.6 |

Example 19

The same UF-system as in example 17 was used for concentration of rFVIIa bulk without diafiltration. Before concentration, the volume of the rFVIIa bulk was 188 mL and the concentration of rFVIIa was 1.1 mg/mL in a buffer with 50 mM NaCl, 10 mM $CaCl_2$, 10 mM Glycyl-glycin, pH 6.81.

Sucrose was added to a final concentration of 3% (w/w). After concentration by UF, the volume of the solution was 25 mL and the concentration of rFVIIa was 8.3 mg/mL as measured by $OD_{280}$ and 8.8 as measured by SEC-HPLC. No significant change was seen in the levels of heavy chain degradation, GD-FVIIa, polymers or oligomers/dimers from before UF to after UF (Table 5).

TABLE 5

Results of analyses before and after addition of sucrose and concentration by UF.

| Sample | Heavy chain degradation, % | GD-FVIIa, % | Oxidation % | Polymers, % | Oligomers/ dimers, % | Concentration of rVIIa, mg/mL |
|---|---|---|---|---|---|---|
| Bulk before ultra filtration | 11.5 | 4.6 | 0.02 | 0.02 | 0.4 | 1.1 |
| Bulk after ultra filtration | 11.9 | 4.9 | 0.02 | 0.02 | 0.5 | 8.8 |

Example 20

A concentration of rFVIIa from 1.5 mg/mL to 12.0 mg/mL was performed as in example 19, but with 3% (w/w) mannitol added instead of sucrose. The solution was visually clear during the concentration and no significant change was seen in the levels of heavy chain degradation, oxidation, GD-FVIIa, polymers or oligomers/dimers from before UF to after UF.

Example 21

The same UF-system as in example 17 was used for concentration of rFVIIa bulk without diafiltration. Before concentration, the volume of the rFVIIa bulk was 203 mL and the concentration of rFVIIa was 1.3 mg/mL in a buffer with 50 mM NaCl, 10 mM $CaCl_2$, 10 mM Glycyl-glycin, pH 6.62. NaCl was added, so that the final concentration of NaCl was enhanced to a total of 100 mM. After concentration by UF, the volume of the solution was 19 mL and the concentration of rFVIIa was 11.6 mg/mL as measured by $OD_{280}$ and 11.7 as measured by SEC-HPLC. No significant change was seen in the levels of heavy chain degradation, GD-FVIIa, polymers or oligomers/dimers from before UF to after UF (Table 6).

TABLE 6

Results of analyses before and after addition of NaCl and concentration by UF.

| Sample | Heavy chain degradation, % | GD-FVIIa, % | Oxidation % | Polymers, % | Oligomers/ dimers, % | Concentration of rVIIa, mg/mL |
|---|---|---|---|---|---|---|
| Bulk before ultra filtration | 11.0 | 4.8 | 2.2 | 0.07 | 0.5 | 1.3 |
| Bulk after ultra filtration | 11.7 | 5.3 | 2.2 | 0.02 | 0.7 | 11.7 |

Example 22

The same UF-system as in example 17 was used for concentration of rFVIIa bulk without diafiltration. Before UF, the bulk contained 1.42 mg/mL of rFVIIa in a buffer with 50 mM NaCl, 10 mM $CaCl_2$, 10 mM Glycylglycine, pH 6.0. $CaCl_2$ was added, so that the final concentration of $CaCl_2$ was enhanced to a total of 30 mM. The bulk was concentrated on the UF-system until a concentration of 25.3 mg/mL as measured by $OD_{280}$ and 24.1 mg/mL as measured by SEC-HPLC. The solution was visually clear during the concentration, and $OD_{600}$ only increased to 0.014 at the end of the concentration. No significant change was seen in the levels of heavy chain degradation, oxidation, GD-FVIIa, polymers or oligomers/ dimers from before UF to after UF (table 6).

TABLE 6

Results of analyses before and after addition of CaCl₂ and concentration by UF.

| Sample | Heavy chain degradation % | Oxidation % | GD-FVIIa % | Polymers % | Oligomers/ dimers % | Concentration of rVIIa mg/mL |
|---|---|---|---|---|---|---|
| Bulk before ultra filtration | 10.3 | 1.7 | 5.2 | 0.02 | 0.6 | 1.4 |
| Bulk after ultra filtration | 10.2 | 1.6 | 5.1 | 0.02 | 0.7 | 24.1 |

Example 23

A Labscale TFF System (Millipore), equipped with a Pellicon XL Filter Device with Biomax 30 kD membrane (Millipore no. PXB030A50) was used for ultrafiltration (UF) of 234 mL rFVIIa bulk. The UF was performed at 2-8° C. with a flow across the membrane of 20-30 mL/minute, and an inlet pressure of 1-1.5 bar. Before UF, the bulk contained 1.3 mg/mL of rFVIIa in a buffer with 50 mM NaCl, 10 mM CaCl₂, 10 mM Glycylglycine, pH 5.53. The bulk was concentrated on the UF-system and during the concentration the appearance was inspected and samples were measured for clarity by OD₆₀₀. When the bulk was concentrated to 42 mL (calculated concentration 7.2 mg/mL), the solution became visually unclear, and a precipitate was formed in a sample that was left overnight at 2-8° C. When the solution was further concentrated to 34 mL (calculated concentration 8.9 mg/mL), precipitates was clearly seen. OD₆₀₀ increased slightly during the first part of the concentration, but increased abruptly when the concentrated solution was down to 34 mL (FIG. 1).

In all the above examples relating to ultrafiltration, no significant change in specific activity (IU per µg of the Factor VII polypeptide) measured by the clot assay (Assay 4) was observed.

Manufacturing of Compositions and Stability

Example 24

In order to investigate the stability of a concentrated rFVIIa formulation the following composition was manufactured:

15 mg/mL rFVIIa (corresponding to 3.9 mg rFVIIa per mL vial volume)

1.55 mg/mL Histidine 1.32 mg/mL Glycylglycine 5.84 mg/mL Sodium chloride 1.47 mg/mL Calcium chloride 25.0 mg/mL Mannitol 10.0 mg/mL Sucrose 0.07 mg/mL Tween 80 pH=5.50

The composition was prepared from a purified bulk solution (15.6 mg/mL). Excipients were added to the bulk solution, the resulting solution was sterile filtered using a sterilised membrane filter (0.2 micron pore size or equivalent). 1.0 mL of the resulting solution was filled into sterile glass vials (approx. 3.86 mL). The vials were freeze-dried, stoppered and sealed with aluminium flip-off type caps.

The stability was followed at 25° C.:

| Analysis | Storage time at 25° C. (months) | | | | |
|---|---|---|---|---|---|
| | 0 | 1 | 2 | 3 | 6 |
| Dimers/ Oligomers (%) | 3.9 | 3.8 | 3.9 | 4.6 | 3.9 |
| Polymers (%) | <0.3 | <0.3 | <0.3 | <0.3 | <0.3 |
| Heavy chain degradation (%) | 12.2 | 11.5 | 11.7 | 11.6 | 11.6 |
| Oxidation (%) | 3.0 | 2.0 | 2.2 | 2.1 | 2.3 |
| Clot activity (IU/mL) | 788,500 | 699,600 | 718,400 | 866,600 | 934,400 |

| Analysis | Storage time at 25° C. (months) | |
|---|---|---|
| | 9 | 12 |
| Dimers/Oligomers (%) | 3.2 | 2.6 |
| Polymers (%) | <0.3 | <0.3 |
| Heavy chain degradation (%) | 11.9 | 11.6 |
| Oxidation (%) | 2.4 | 2.6 |
| Clot activity (IU/mL) | 749,700 | 770,700 |

The stability was followed at 40° C.:

| Analysis | Storage time at 40° C. (months) | | | |
|---|---|---|---|---|
| | 0 | 1 | 2 | 3 |
| Dimers/Oligomers (%) | 3.9 | 4.2 | 4.2 | 4.8 |
| Polymers (%) | <0.3 | <0.3 | <0.3 | <0.3 |
| Heavy chain degradation (%) | 12.2 | 11.5 | 11.7 | 11.6 |
| Oxidation (%) | 3.0 | 2.2 | 2.4 | 2.3 |
| Clot activity (IU/mL) | 788,500 | 734,500 | 736,800 | 719,700 |

Example 25

In order to investigate the stability of a concentrated rFVIIa formulation the following composition was manufactured:

20 mg/mL rFVIIa (corresponding to 13.0 mg rFVIIa per mL vial volume)

2.34 mg/mL Sodium chloride 1.55 mg/mL Histidine 5.15 mg/mL Calcium chloride 2H₂0

25.0 mg/mL Mannitol 10.0 mg/mL Sucrose 0.07 mg/mL Tween 80

0.5 mg/ml Methionine pH=6.00

The composition was prepared from a purified bulk solution (20 mg/mL). Excipients were added to the bulk solution, the resulting solution was sterile filtered using a sterilised membrane filter (0.2 micron pore size or equivalent). 2.5 mL of the resulting solution was filled into sterile glass vials (approx. 3.86 mL). The vials were freeze-dried, stoppered and sealed with aluminium flip-off type caps.

The stability was followed at 25° C.:

| | Storage time at 25° C. (months) | |
|---|---|---|
| Analysis | 0 | 3 |
| Dimers/Oligomers (%) | 3.5 | 3.7 |
| Polymers (%) | ≤0.1 | 0.1 |
| Heavy chain degradation (%) | 9.2 | 9.1 |
| Oxidation (%) | 1.3 | 1.5 |
| Clot activity (IU/mL) | 1097500 | 988500 |

Example 26

In order to investigate the stability of a concentrated rFVIIa formulation the following composition was manufactured:
20 mg/mL rFVIIa (corresponding to 20 mg rFVIIa per mL cartridge volume)
1.55 mg/mL Histidine
5.15 mg/mL Calcium chloride $2H_2O$
1.22 mg/mL Inhibitor 0008
pH=6.50

The composition was prepared from a purified bulk solution (20 mg/mL). Excipients were added to the bulk solution, the resulting solution was sterile filtered using a sterilised membrane filter (0.2 micron pore size or equivalent). 3.0 mL of the resulting solution was filled into a sterile glass cartridge (approx. 3.0 mL) and sealed with aluminium cap.

The stability was followed at 5° C.:

| | Storage time at 5° C. (months) | | | |
|---|---|---|---|---|
| Analysis | 0 | 1 | 2 | 3 |
| Heavy chain degradation (%) | 8.6 | 8.5 | 8.7 | 9.1 |
| Oxidation (%) | 1.1 | 1.2 | 1.3 | 1.7 |
| Clot activity (IU/mL) | 932600 | 1019300 | 1017700 | 1022700 |

Example 27

In order to investigate the stability of a concentrated rFVIIa formulation the following composition was manufactured:
5 mg/mL rFVIIa (corresponding to 5 mg rFVIIa per mL cartridge volume)
1.55 mg/mL Histidine
122.5 mg/mL Calcium chloride $2H_2O$
2.45 mg/ml Sodium acetate
pH=6.50

The composition was prepared from a purified bulk solution (7.1 mg/mL). Excipients were added to the bulk solution, the resulting solution was sterile filtered using a sterilised membrane filter (0.2 micron pore size or equivalent). 3.0 mL of the resulting solution was filled into a sterile glass cartridge (approx. 3.0 mL) and sealed with aluminium cap.

The stability was followed at 5° C.:

| | Storage time at 5° C. (months) | | | | | |
|---|---|---|---|---|---|---|
| Analysis | 0 | 1 | 2 | 3 | 6 | 12 |
| Clot activity (IU/mL) | 267,500 | 260,500 | 241,100 | 258,900 | 229,300 | 205,800 |

The invention claimed is:

1. A process for the preparation of a concentrated solution of activated recombinant Factor VII polypeptide, said solution comprising in the range of from about 16 to about 25 mg of the activated Factor VII polypeptide per mL volume of a closed container, wherein, said process comprises the steps of:
   (a) contacting a solution comprising a recombinant Factor VII polypeptide with an anion-exchange material under conditions which facilitate binding of a portion of said Factor VII polypeptide to said anion-exchange material said Factor VII solution having a pH in the range of 5.5-7.0, or a pH in the range of 8.5-9.5 with the presence of at least 15 mM $Ca^{2+}$;
   (b) washing said anion-exchange material with a washing buffer having a pH in the range of 5.5-7.0; and
   (c) eluting said anion-exchange material with an elution buffer having a pH in the range of 3.0-7.0, and comprising calcium ions ($Ca^{+2}$) in a concentration of at least 15 mM; and collecting the eluate of the activated Factor VII polypeptide;
   (d) loading at least a portion of the eluate into a container so that the container comprises in the range of from about 16 to about 25 mg of the activated Factor VII polypeptide per mL volume of the container;
   (e) optionally lyophilizing the eluate; and
   (f) sealing the container so as to provide a closed container.

2. Process according to claim 1, wherein the elution buffer of step (c) comprises 15-50 mM $Ca^{2+}$.

3. Process according to claim 1, wherein the elution buffer of step (c) is a gradient buffer with respect to $Ca^{2+}$ wherein the initial concentration of Ca2+ is in the range of 15-20 mM and the final concentration of Ca2+ is in the range of 15-100 mM.

4. Process according to claim 1, wherein the elution buffer of step (c) further comprises one or more mono-, di- or trivalent anions selected from the group of: chloride, acetate, malonate, phosphate, carbonate, sulphate, and nitrate.

5. Process according to claim 3, wherein the elution buffer of step (c) comprises chloride anions ($Cl^-$) in a concentration of 100-800 mM.

6. Process according to claim 1, wherein the elution buffer of step (c) has an ionic strength of 100-1000 mM.

7. A process according to claim 1, wherein the washing buffer of step (b) further comprises salts corresponding to an ionic strength of 40-250 mM.

8. A process according to claim 1, wherein the anion-exchange material of step (a) is a hydroxyapatite material.

9. A method for obtaining a concentrated solution of an activated recombinant Factor VII polypeptide, said method comprising the steps of:
   (a) contacting a solution comprising a recombinant Factor VII polypeptide with an anion-exchange material under conditions which facilitate binding of a portion of said Factor VII polypeptide to said anion-exchange material, said Factor VII solution having a pH in the range of 5.5-7.0, or alternatively a pH in the range of 8.5-9.5 with the presence of at least 15 mM $Ca^{2+}$;

(b) washing said anion-exchange material with a washing buffer having a pH in the range of 5.5-7.0; and
(c) eluting said anion-exchange material with an elution buffer having a pH in the range of 3.0-7.0, and comprising calcium ions ($Ca^{2+}$) in a concentration of at least 15 mM; and collecting the eluate of the activated Factor VII polypeptide;
wherein the concentrated solution of the activated Factor VII polypeptide obtained has a concentration from about 16 to about 25 mg per mL.

10. Method according to claim 9, wherein the elution buffer of step (c) comprises 15-50 mM $Ca^{2+}$.

11. Method according to claim 9, wherein the elution buffer of step (c) is a gradient buffer with respect to $Ca^{2+}$ wherein the initial concentration of $Ca2+$ is in the range of 15-20 mM and the final concentration of $Ca2+$ is in the range of 15-100 mM.

12. Method according to claim 9 wherein the elution buffer of step (c) further comprises one or more mono-, di- or trivalent anions selected from the group of: chloride, acetate, malonate, phosphate, carbonate, sulphate, and nitrate.

13. Method according to claim 12, wherein the elution buffer of step (c) comprises chloride anions ($Cl^-$) in a concentration of 100-800 mM.

14. Method according to claim 9, wherein the elution buffer of step (c) has an ionic strength of 100-1000 mM.

15. Method according to claim 9, wherein the washing buffer of step (b) further comprises salts corresponding to an ionic strength of 40-250 mM.

16. Method according to claim 9, wherein the anion-exchange material of step (a) is a hydroxyapatite material.

* * * * *